United States Patent [19]

Campbell et al.

[11] Patent Number: 4,783,467
[45] Date of Patent: Nov. 8, 1988

[54] TETRAHYDROIMIDAZOQUINAZOLINONE INOTROPIC AGENTS

[75] Inventors: Simon F. Campbell, Deal; David A. Roberts, Sandwich, both of England

[73] Assignee: Pfizer Inc., New York, N.Y.

[21] Appl. No.: 865,693

[22] Filed: May 22, 1986

[30] Foreign Application Priority Data

Jun. 5, 1985 [GB] United Kingdom ............... 8514207
Nov. 5, 1985 [GB] United Kingdom ............... 8527208

[51] Int. Cl.$^4$ .................. A61K 31/505; C07D 487/04
[52] U.S. Cl. .................................... 514/267; 514/254; 544/238; 544/250
[58] Field of Search ............... 544/250, 238; 514/267, 514/254

[56] References Cited

U.S. PATENT DOCUMENTS

| | | | |
|---|---|---|---|
| 3,932,407 | 1/1976 | Beverung, Jr. et al. | 544/250 |
| 3,983,119 | 9/1976 | Beverung, Jr. et al. | 544/250 |
| 3,983,120 | 9/1976 | Beverung et al. | 544/250 |
| 4,208,521 | 6/1980 | Crenshaw et al. | 544/250 |
| 4,256,748 | 3/1981 | Chodnekar et al. | 514/267 |
| 4,593,029 | 6/1986 | Venuti et al. | 514/267 |
| 4,596,806 | 6/1986 | Ishikawa et al. | 514/267 |
| 4,610,987 | 9/1986 | Ishikawa | 514/239 |

FOREIGN PATENT DOCUMENTS

| | | | |
|---|---|---|---|
| 1131631 | 9/1982 | Canada | 514/267 |
| 0021338 | 1/1981 | European Pat. Off. | 514/267 |
| 0054180 | 6/1982 | European Pat. Off. | 544/250 |
| 0129258 | 12/1984 | European Pat. Off. | |
| 0133234 | 2/1985 | European Pat. Off. | |
| 0205280 | 12/1986 | European Pat. Off. | 544/250 |
| 2001638 | 2/1979 | United Kingdom | 514/267 |

*Primary Examiner*—Donald G. Daus
*Assistant Examiner*—Diana G. Rivers
*Attorney, Agent, or Firm*—Peter C. Richardson; Paul H. Ginsburg; J. Trevor Lumb

[57] ABSTRACT

A series of novel heterocyclic-substituted 1,2,3,5-tetrahydroimidazo(2,1-b)quinazolin-2-(1H)-one compounds have been prepared, including their pharmaceutically acceptable salts, wherein the heterocyclic ring moiety is an optionally substituted 5- or 6-membered aromatic heterocyclic group attached to the 6-, 7-, 8- or 9-positions of the aforesaid tetrahydroquinaxolinone ring. These particular compounds are useful in therapy as highly potent inotropic and therefore, are of value in the treatment of various cardiac conditions. Preferred member compounds include 7-(2,4-dimethylimidaxol-1-yl)-9-methyl-1,2,4,5,-tetrahydroimidazo (2,1-b)quinazolin-2-(1H)-one, 3,9-dimethyl-7-(2,4-dimethylimidazol-1-yl) -1,2,3,5-tetrahydroimidazo(2,1-b)quinazolin-2-(1H)-one and 9-methyl-7 -(1,2,4-triazol-4-yl)-1,2,3,5-tetrahydroimidazo(2,1-b)quinazolin-2-(1H)-one, respectively. Methods for preparing these compounds from known starting materials are provided.

21 Claims, No Drawings

TETRAHYDROIMIDAZOQUINAZOLINONE INOTROPIC AGENTS

BACKGROUND OF THE INVENTION

This invention relates to substituted 1,2,3,5-tetrahydroimidazo[2,1-b]quinazolin-2-(1H)-one cardiac stimulant agents which in general selectively increase the force of myocardial contraction without producing significant increases in heart rate. The compounds are useful in the curative or prophylactic treatment of cardiac conditions, in particular in the treatment of heart failure.

SUMMARY OF THE INVENTION

Thus according to the invention there are provided substituted 1,2,3,5-tetrahydroimidazo(2,1-b)quinazolin-2-(1H)-ones of the formula:

(I)

and their pharmaceutically acceptable salts, wherein "Het" is an optionally substituted 5- or 6-membered aromatic heterocyclic group attached to the 6-, 7-, 8-, or 9-position of said 1,2,3,5-tetrahydroimidazo[2,1-b]quinazolin-2-(1H)-one; R, which is attached to the 6-, 7-, 8- or 9-position, is hydrogen, $C_1$–$C_4$ alkyl, $C_1$–$C_4$ alkoxy, hydroxy, hydroxymethyl, halo or $CF_3$; and $R^1$, $R^2$, $R^3$, $R^4$ and $R^5$ are each H or $C_1$–$C_4$ alkyl.

Preferably "HET" contains 1, 2, 3 or 4 nitrogen atoms in the aromatic ring which is attached to the 1,2,3,5-tetrahydroimidazo(2,1-b)quinazolin-2-(1H)one by a carbon or nitrogen atom of the heterocyclic ring.

Examples of said group "Het" in the formula (I) include, for example, pyrrolyl, imidazolyl, pyrazolyl, triazolyl, tetrazolyl, pyridyl, pyrazinyl, pyrimidinyl, pyridazinyl, oxazolyl, isoxazolyl, thiazolyl, isothiazolyl, furyl, thienyl, oxadiazolyl, and, when nitrogen containing, their N-oxides, all being optionally substituted by up to 3, preferably by 1 or 2, substituents each independently selected from, e.g., $C_1$–$C_4$ alkyl, $C_1$–$C_4$ alkoxy, hydroxy, halo, $CF_3$, cyano, hydroxymethyl, ($C_1$–$C_4$ alkoxy)carbonyl, $—NO_2$, $—NR^6R^7$, $—CONR^6R^7$, $—SO_2NR^6R^7$ and $—S(O)_m(C_1$–$C_4$ alkyl) where $R^6$ and $R^7$ are each independently H or $C_1$–$C_4$ alkyl and m is 0, 1 or 2.

"Halo" means F, Cl, Br or I. $C_3$ and $C_4$ alkyl and alkoxy groups can be straight or branched chain. The preferred alkyl group is methyl.

Although the compounds of the formula (I) are written as 1,2,3,5-tetrahydroimidazo(2,1-b)quinazolin-2-(1H)-ones, it should be realised that the following tautomerism will occur when $R^5$ is H:

(Ia) ⇌ (Ib) ⇌ (Ic)

However, as the keto-form (Ia) is considered the most stable tautomer, the end products herein will be named and illustrated as 1,2,3,5-tetrahydroimidazo(2,1-b)quinazolin-2-(1H)-ones although those skilled in the art will realise that all three tautomers may be present or that any particular compound so named may exist predominantly as (Ib) or (Ic) and the following disclosure is to be interpreted to incorporate all tautomeric forms. Similarly, compounds having a hydroxy substituent on "Het" may be tautomeric with their oxo analogues and again such tautomers are incorporated.

R is preferably H or $C_1$–$C_4$ alkyl, more preferably H or $CH_3$.

When R is a substituent it is preferably in the 9-position.

R is most preferably 9-$CH_3$.

$R^1$ is preferably H or $C_1$–$C_4$ alkyl, more preferably H or $CH_3$.

$R^1$ is most preferably H.

$R^2$ is preferably H.

$R^3$ is preferably H or $CH_3$. Most preferably, $R^3$ is H.

$R^4$ is preferably H or $CH_3$. Most preferably, $R^3$ is H.

$R^4$ is preferably H or $CH_3$. Most preferably, $R^4$ is H.

$R^5$ is preferably H.

"Het" is preferably attached to the 7-position.

"Het" is preferably an imidazolyl, triazolyl or pyridyl group optionally substituted as defined above. "Het" is more preferably an imidazolyl (especially imidazol-1-yl), triazolyl (especially 1,2,4-triazol-1-yl, 1,2,4-triazol-4-yl or 1,2,4-triazol-5-yl) or pyridyl (especially pyrid-3-yl or pyrid-5-yl) group, said imidazolyl and triazolyl groups being optionally substituted by 1 or 2 $C_1$–$C_4$ alkyl (especially methyl) groups, and said pyridyl group being optionally substituted by 1 or 2 $C_1$–$C_4$ alkyl (especially methyl) groups or by a single hydroxy group. Most preferably, "Het" is a 2,4-dimethylimidazol-1-yl, 1,2,4-triazol-1-yl, 1,2,4-triazol-4-yl, 1-methyl-1,2,4-triazol-5-yl, 2,6-dimethylpyrid-3-yl or 2-hydroxypyrid-5-yl group.

The most preferred individual compounds have the formula:

wherein:
(a) "Het" is 2,4-dimethylimidazol-1-yl and $R^3$ and $R^4$ are H;
(b) "Het" is 2,4-dimethylimidazol-1-yl, $R^3$ is $CH_3$ and $R^4$ is H; or "Het" is 1,2,4-triazol-4-yl and $R^3$ and $R^4$ are H.

The compound of (a) above is especially preferred.

The pharmaceutically acceptable salts of the compounds of the formula (I) are preferably acid addition salts formed from acids which form non-toxic acid addition salts containing pharmaceutically acceptable anions, such as hydrochloride, hydrobromide, hydroiodide, sulphate or bisulphate, phosphate or hydrogen phosphate, acetate, maleate, fumarate, lactate, tartrate, citrate, gluconate, p-toluenesulphonate, and methanesulphonate salts. Also included are the metal salts, especially the alkali metal and alkaline earth metal salts, preferably the sodium and potassium salts.

The cardiac stimulant activity of the compounds of the formula (I) is shown by their effectiveness in one or more of the following tests: (a) increasing the force of contraction in the "Starling" dog heart-lung preparation measured via a left ventricular catheter; (b) increasing myocardial contractility (left ventricular dp/dt max.) in the anaesthetised dog measured via a left ventricular catheter; (c) increasing myocardial contractility in the conscious dog with an implanted left ventricular transducer (dp/dt max.) or an exteriorised carotid artery loop (systolic time intervals).

In test (a), the positive inotropic effect of the test compound following bolus administration is measured in the "Starling" dog heart-lung preparation. The selectivity for increase in force versus frequency of contraction of the test compound is obtained.

In test (b), the positive inotropic action of the test compound following intravenous administration is measured in the anaesthetised dog. The magnitude and duration of this action, and the selectivity for increase in force versus frequency of contraction of the test compound are obtained, as are the peripheral effects, e.g. the effect on blood pressure.

In test (c) the positive inotropic action of the test compound following intravenous or oral administration to a conscious dog with an implanted left ventricular transducer (dp/dt max.) or an exteriorised carotid artery loop (systolic time intervals) is measured. The magnitude of the inotropic action, the selectivity for increase in force versus frequency of contraction, and the duration of action of the inotropic effect of the test compound are all obtained.

The compounds of the formula (I) and their salts can be administered alone but will generally be administered in admixture with a pharmaceutical carrier selected with regard to the intended route of administration and standard pharmaceutical practice. For example they may be administered orally in the form of tablets containing such excipients as starch or lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic.

For administration to man in the curative or prophylactic treatment of cardiac conditions such as congestive heart failure, it is expected that oral dosages of the compounds of the formula (I) will be in the range from 10 mg to 1 g daily, taken in 1 to 4 divided doses per day, for an average adult patient (70 kg). Dosages for intravenous administration would be expected to be within the range 0.5 to 100 mg per single dose as required, for example in the treatment of acute heart failure. Thus for a typical adult patient, individual tablets or capsules might contain 2.5 to 250 mg of active compound, in a suitable pharmaceutically acceptable vehicle or carrier. Variations may occur depending on the weight and condition of the subject being treated as will be known to medical practitioners.

Thus the present invention provides a pharmaceutical composition comprising a compound of the formula (I) as defined above or pharmaceutically acceptable salt thereof, together with a pharmaceutically acceptable diluent or carrier.

The invention also provides a method of stimulating the heart of an animal, including a human being, which comprises administering to the animal a compound of formula (I) or pharmaceutically acceptable salt thereof, or a pharmaceutical composition as defined above, in an amount sufficient to stimulate the heart of the animal.

The invention yet further provides a compound of the formula (I) or pharmaceutically acceptable salt thereof, for use as a medicament, in particular for use in stimulating the heart of a human being suffering from congestive heart failure.

The invention also includes any novel intermediates described herein, such as those of the formulae (II), (III) and (IV).

DETAILED DESCRIPTION OF THE INVENTION

The compounds of the formula (I) may be prepared by a number of routes, including the following:

Route A:

This route can be illustrated in general terms as follows:

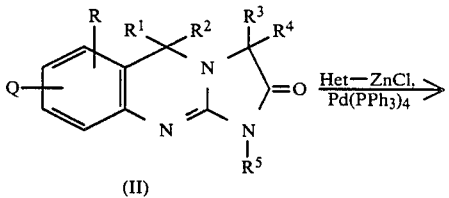

(II)

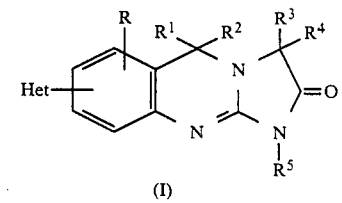

(I)

Q is a suitable leaving group, e.g. Br or I. Q is preferably I. Thus it will be seen that this reaction involves the displacement of the leaving group Q by the heteroaryl zinc chloride with tetrakis (triphenylphosphine) palladium (O) catalysis. The reaction is typically carried out at 25°–80° C., and preferably under reflux, in a suitable organic solvent, e.g. tetrahydrofuran (THF).

Typical reactions are illustrated as follows:

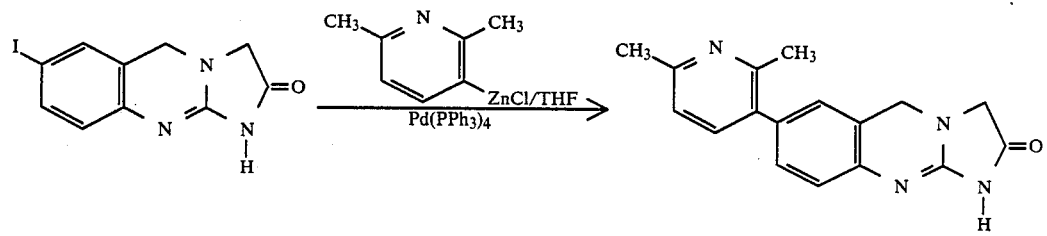

and

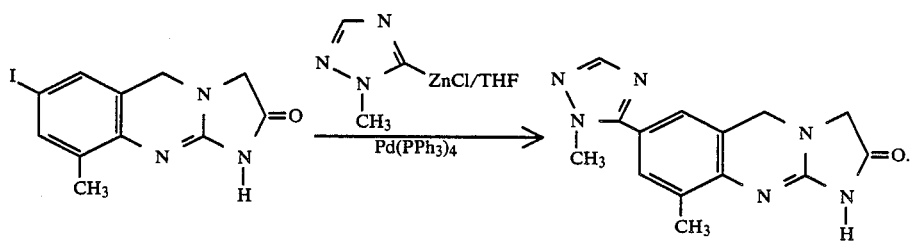

Heteroaryl magnesium chlorides may also be used in place of zinc chlorides using other suitable transition metal catalysts (e.g. nickel-based).

The starting materials used in this method are either known compounds or are obtainable conventionally.

The heteroaryl zinc chlorides are most conveniently obtained in situ by reacting the appropriate haloheterocycle at $-70°$ to $-100°$ C. in THF with two equivalents of t-butyl lithium or one equivalent of n-butyllithium to obtain the lithio derivative, followed by reaction with a solution of anhydrous zinc chloride in THF. In certain cases, the heteroaryl lithium reagents can be prepared by direct lithiation of the parent heterocycle with n-butyl lithium in THF at $-70°$ to $-100°$ C. The heteroaryl zinc chlorides can also be prepared from the corresponding Grignard reagents by reacting them with a solution of zinc chloride in THF.

The desired end product of the formula (I) is then typically obtained by the addition of the appropriate 1,2,3,5-tetrahydroimidazo(2,1-b)quinazolin-2-(1H)-one (II) and tetrakis (triphenylphosphine)palladium (O) in THF and heating under reflux until the reaction is complete, typically in 1 to 48 hours. The product can then be recovered and purified conventionally.

The starting materials of the formula (II) can also be prepared by conventional procedures. Typical routes to these materials, many of which are illustrated in detail in the following Preparations, are as follows:

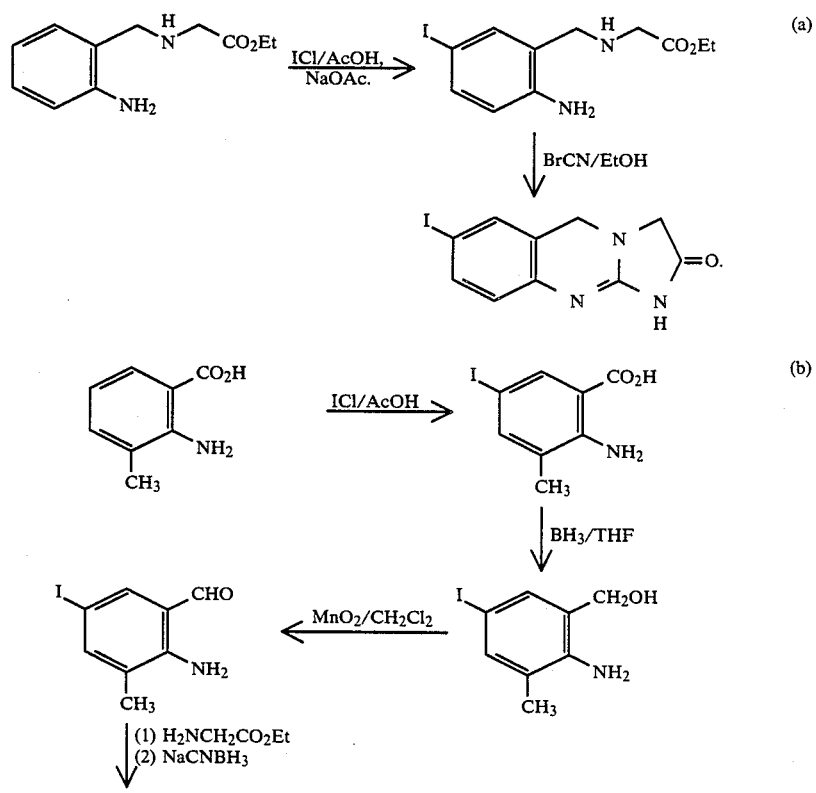

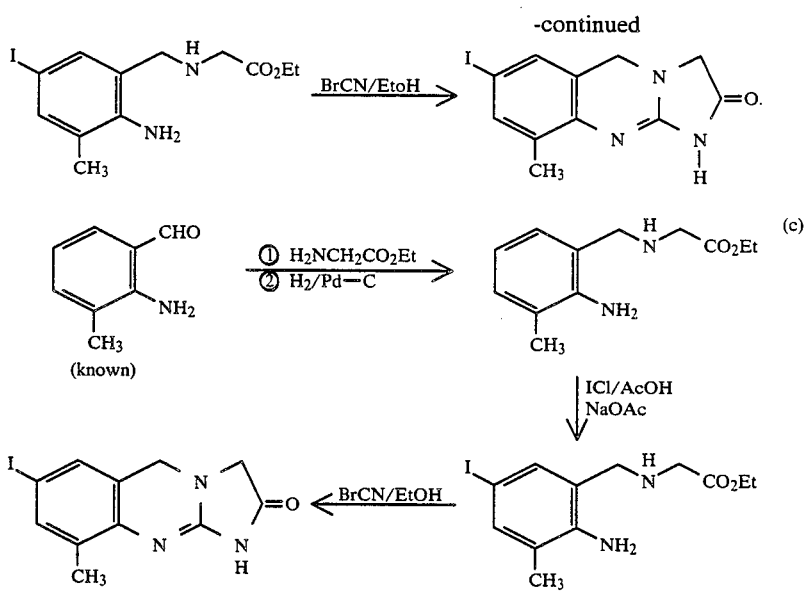

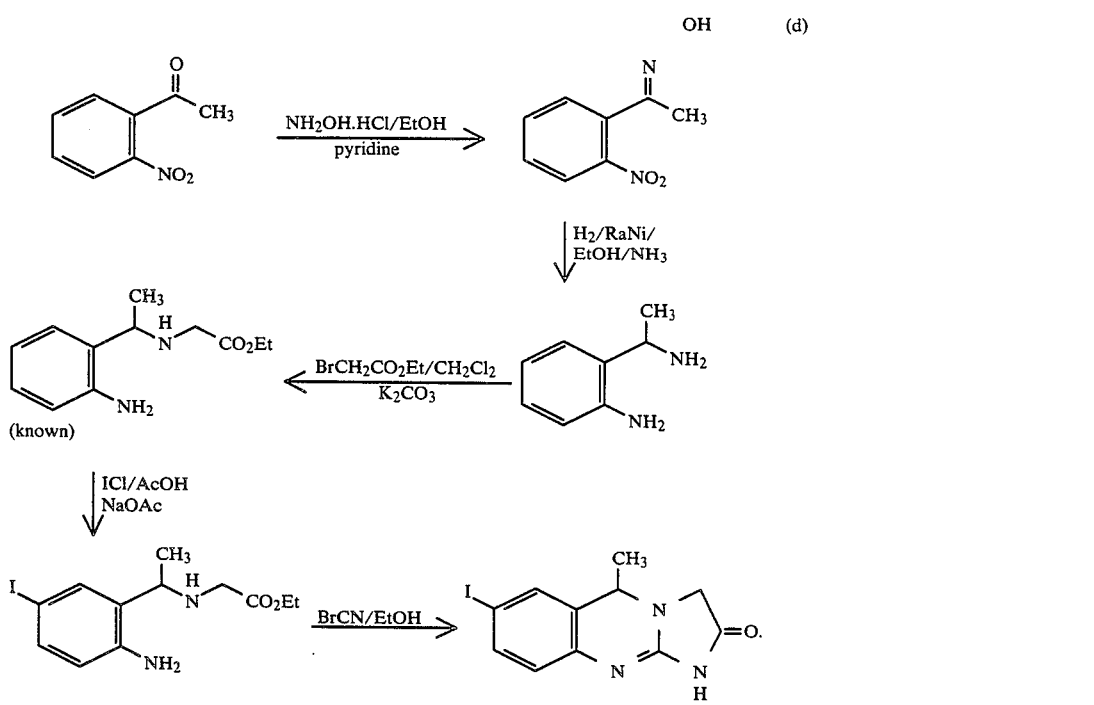

Route B:

This route to compounds in which $R^5$ is H involves the reaction of the starting material (III) with cyanogen bromide or chloride followed by cyclisation of the resulting N-cyano intermediate. The preferred process is illustrated in general terms as follows:

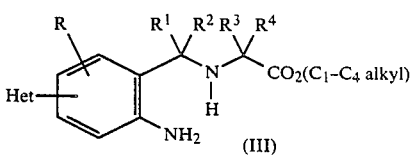

(1) XCN [preferably in ethanol]
(2) Aqueous base [e.g. $Na_2CO_3$, $K_2CO_3$, NaOH]
(3) Cyclisation [typically by reflux in ethanol].

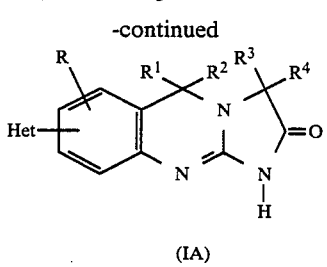

(IA)

X is Cl or Br, and Het, R, $R^1$, $R^2$, $R^3$ and $R^4$ are as defined for formula (I).

Thus the preferred process involves the reaction of the benzylamine derivative (III) with a cyanogen halide, preferably cyanogen bromide, in a suitable organic solvent, e.g. ethanol, typically at 25°–80° C. and preferably under reflux, followed by treatment with an aqueous base, e.g. an aqueous alkali metal base such as sodium carbonate or hydroxide. This usually produces an N-cyano intermediate (see e.g. Example 10) although in some cases partial cyclisation to the next intermediate, a 2-aminoquinazoline, occurs. The N-cyano intermediates have the formula:

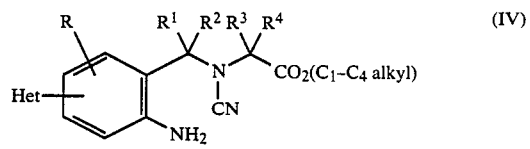

(IV)

where Het, R, $R^1$, $R^2$, $R^3$ and $R^4$ are as previously defined. Cyclisation is then generally completed by heating the intermediate, typically in ethanol or n-butanol, at up to the reflux temperature for 1–72 hours, although in some instances (e.g. in Examples 7–9) cyclisation to the end products (IA) may occur spontaneously without heating. Compound (III) is preferably used as the methyl or ethyl ester.

The product can be isolated and purified conventionally.

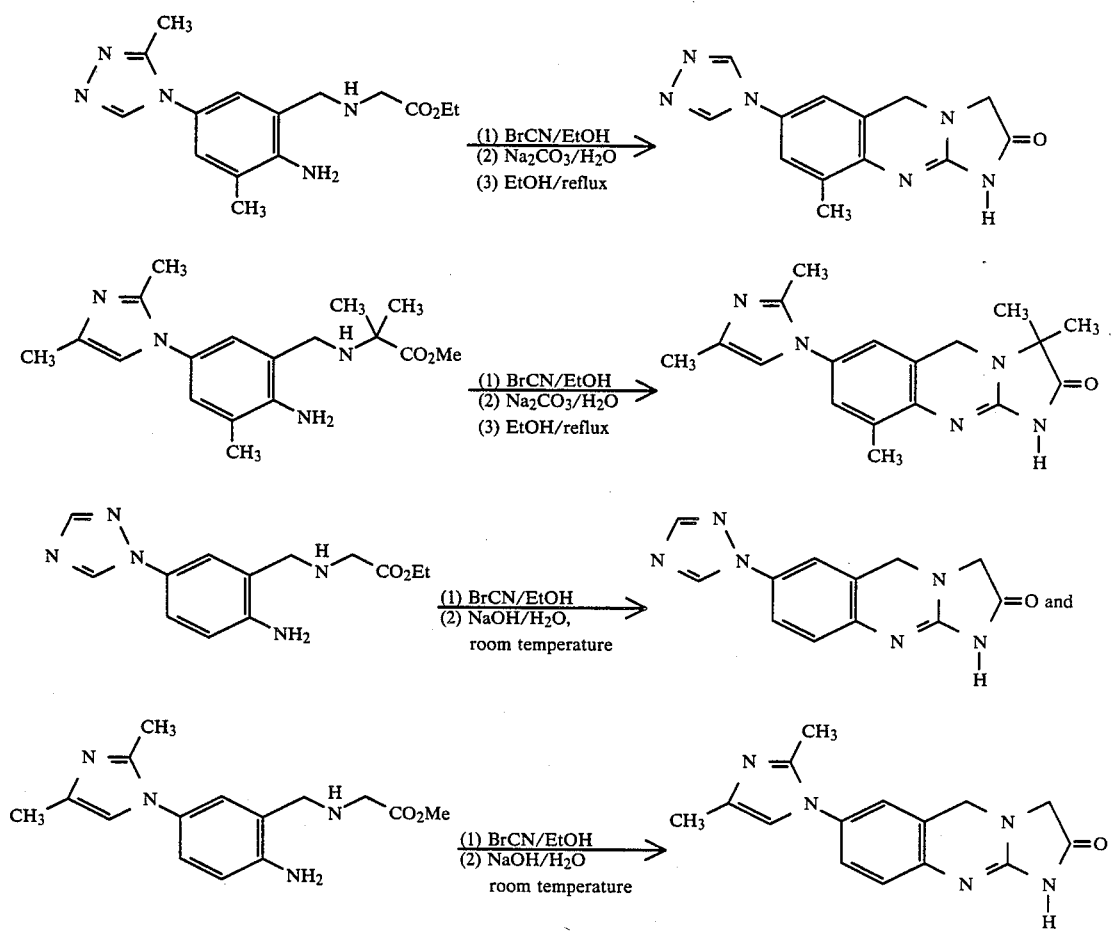

The starting materials for this route can be prepared by conventional procedures. Typical routes to these materials, many of which are illustrated in detail in the following Preparations, are as follows:

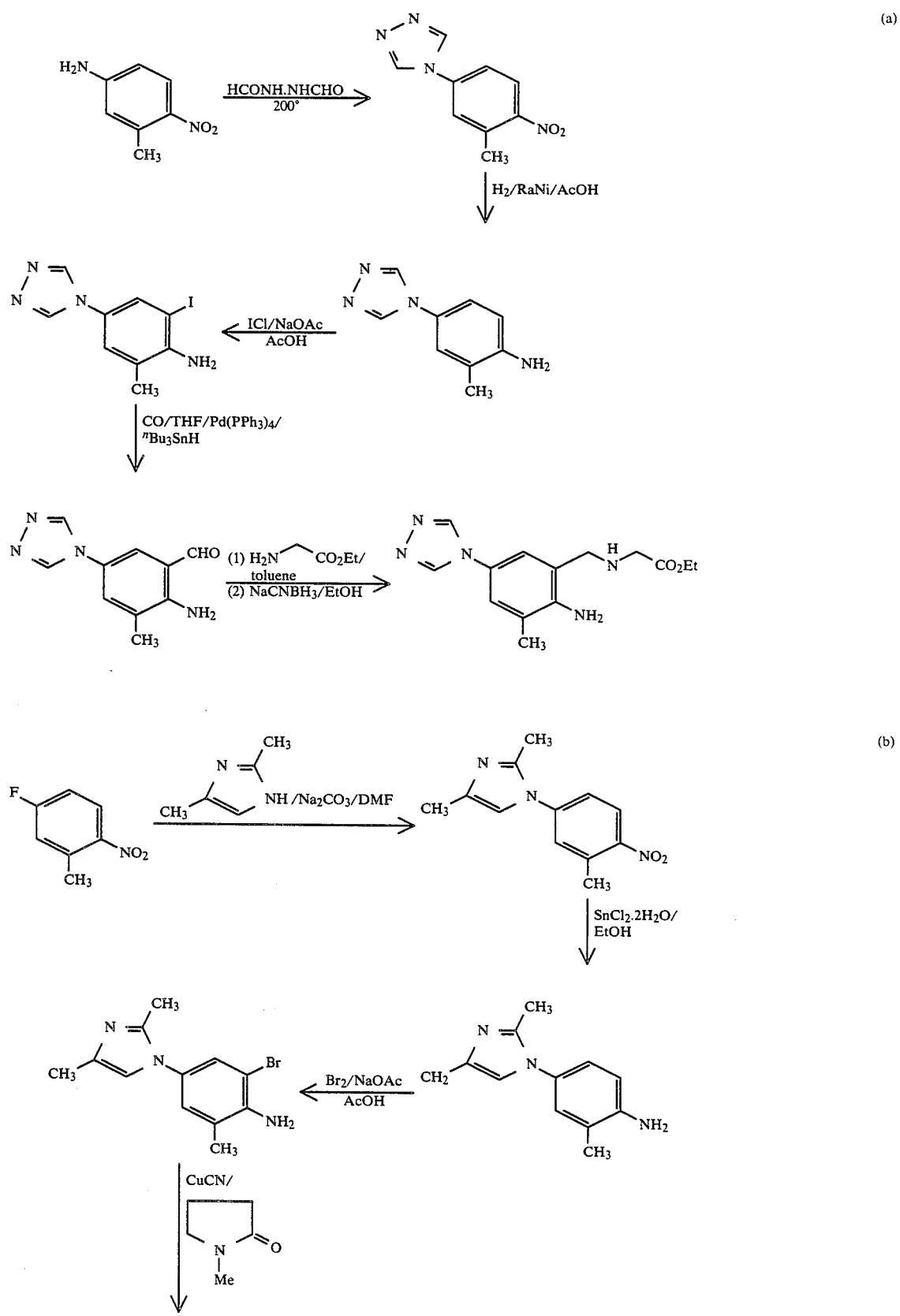

-continued
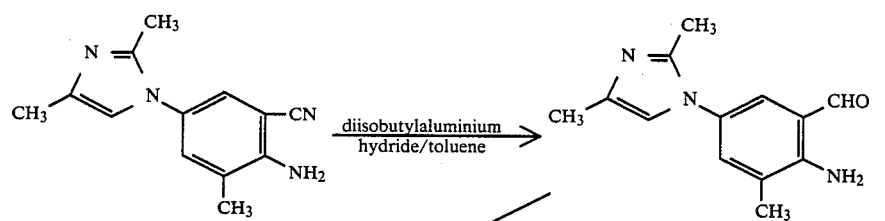
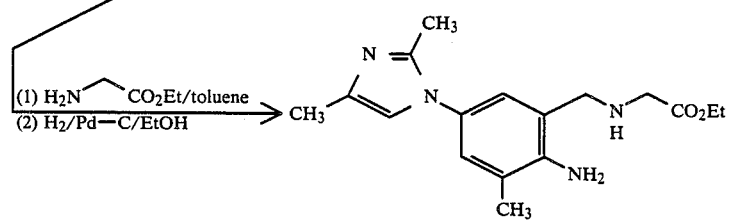
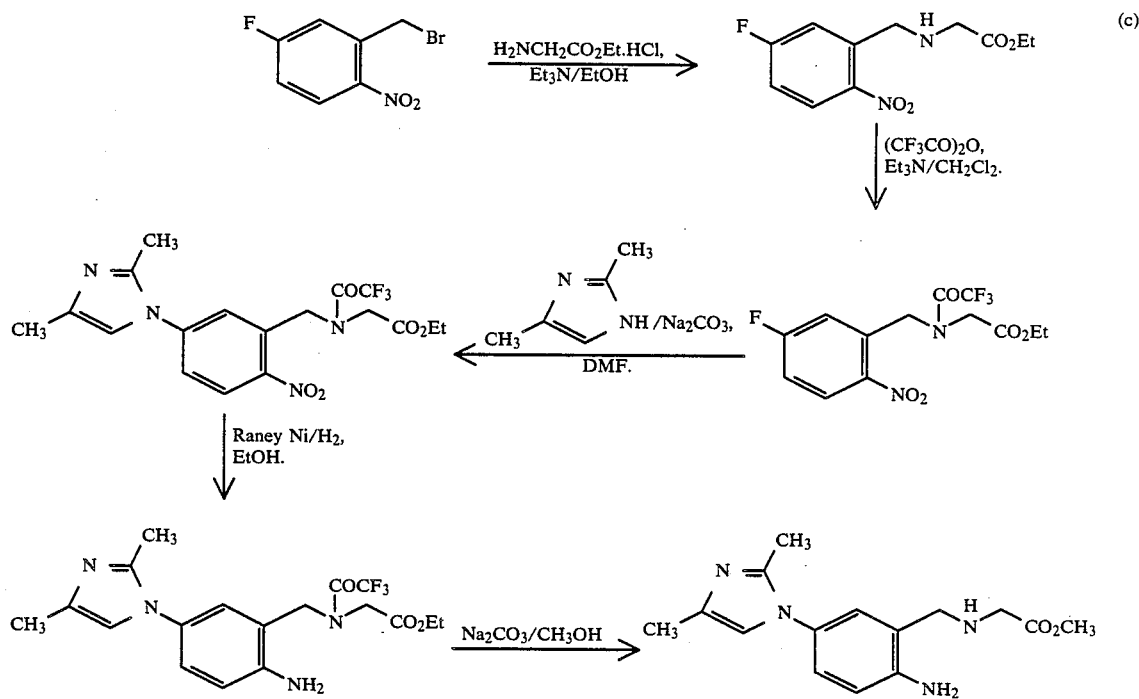
(c)
and
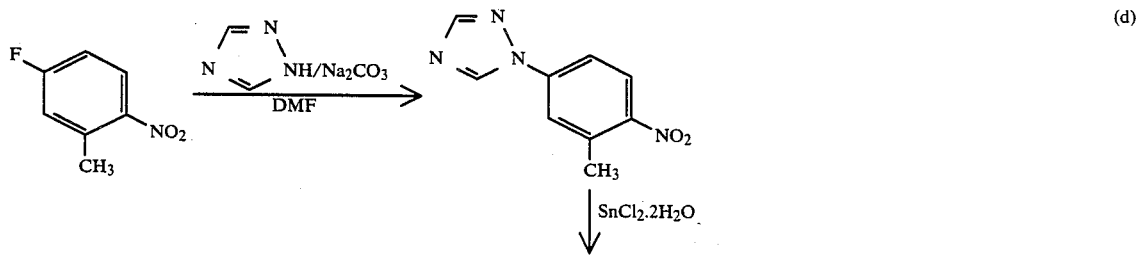
(d)

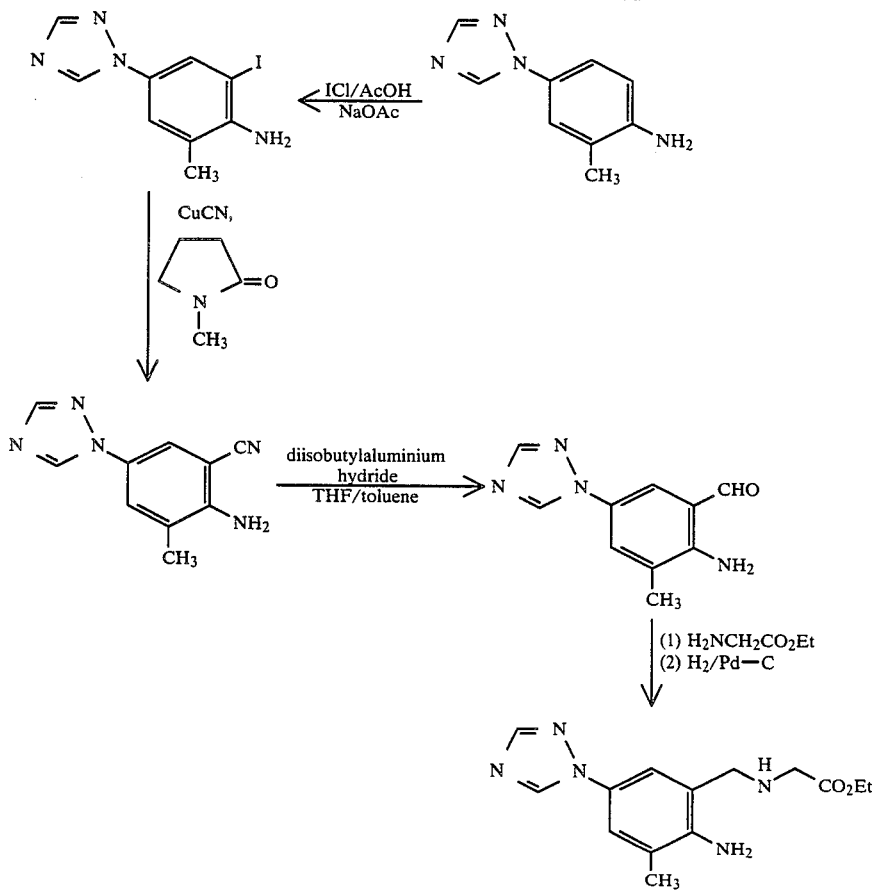

Salts of the compounds of the formula (I) are preparable by conventional methods, e.g. by reacting a solution of the parent compound in an organic solvent with a solution of an appropriate acid in an organic solvent to form an acid addition salt, or by reaction with an appropriate base, e.g. an alkali metal or alkaline earth metal hydroxide, preferably aqueous sodium or potassium hydroxide, to form a pharmaceutically acceptable metal salt.

Where the compounds of the invention contain one or more asymmetric centres, then the invention includes the separated enantiomers and diastereoisomers or mixtures thereof. The separated forms can be obtained by conventional means.

The following Examples illustrate the preparation of the compounds of the formula (I). All temperatures are in °C.:

EXAMPLE 1

7-(2,6-Dimethylpyrid-3-yl)-1,2,3,5-tetrahydroimidazo(2,1-b)quinazolin-2-(1H)-one, 0.5 H$_2$O

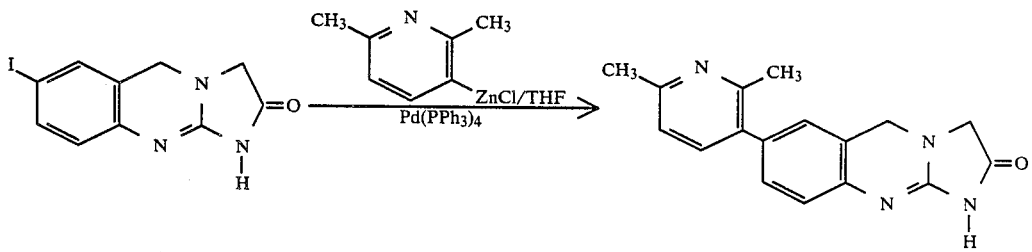

A solution of 3-bromo-2,6-lutidine (1.31 g) in tetrahydrofuran (THF) (3 cm$^3$) was added dropwise to a stirred suspension of magnesium (0.187 g) in THF (4 cm$^3$) under nitrogen at reflux. After ca 20% of the addition a crystal of iodine was introduced and the remainder of the 3-bromo-2,6-lutidine was then added. After a further 0.5 hours at reflux followed by cooling a solution of anhydrous zinc chloride (0.95 g) in THF (5 cm$^3$) was added. A mixture of 7-iodo-1,2,3,5-tetrahydroimidazo(2,1-b)quinazolin-2-(1H)-one (0.94 g) and tetrakis (triphenylphosphine) palladium (O) (0.03 g) was added and the mixture was heated under reflux for 2.5 hours. The cooled solution was evaporated in vacuo and the residue partitioned between chloroform:methanol, 9:1 (100 cm$^3$), and a solution of ethylenediaminetetraacetic acid disodium salt (5.2 g) in water (100 cm³). The organic phase was discarded and the aqueous phase was further extracted with chloroform:methanol, 9:1 (2×50 cm³). The organic phases were again discarded and the aqueous phase was basified to pH9 with saturated sodium carbonate solution, and extracted with chloroform:methanol, 9:1 (4×60 cm³). The combined organic extracts from the last extractions were dried (MgSO₄) and evaporated in vacuo to afford a solid which was chromatographed on silica (Merck "MK 60.9385" [Trade Mark]) eluting with chloroform:methanol, 19:1. Combination and evaporation of the appropriate fractions yielded a solid (0.65 g) which was recrystallised from chloroform-isopropanol to give the title compound, m.p. 330°-332° (0.25 g).

Analysis %:
Found: C,67.9; H,5.5; N,18.9; Calculated for $C_{17}H_{16}N_4O.0.5 H_2O$: C,67.8; H,5.7; N,18.6.

EXAMPLES 2 and 3

The following compounds were prepared similarly to Example 1 starting from the appropriately substituted 7-iodo-1,2,3,5-tetrahydroimidazo(2,1-b)quinazolin-2-(1H)-one, 2,6-dimethylpyrid-3-yl zinc chloride and tetrakis (triphenylphosphine)palladium (O).

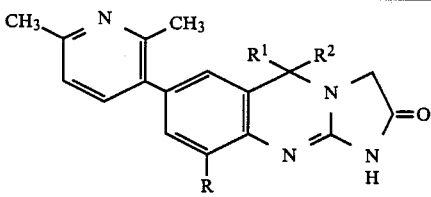

| Example No. | R | R¹ | R² | Form Isolated and m.p. (°C.) | Analysis % (Theoretical in brackets) | | |
|---|---|---|---|---|---|---|---|
| | | | | | C | H | N |
| 2 | —CH₃ | —H | —H | Free base, 253-6° | 70.5 (70.6 | 5.9 5.9 | 18.4 18.3) |
| 3 | —H | —CH₃ | —H | Free base 0.3 H₂O, 314-6° | 69.3 (69.2 | 6.0 6.0 | 17.7 17.9) |

EXAMPLE 4

7-(1-Methyl-1,2,4-triazol-5-yl)-1,2,3,5-tetrahydroimidazo(2,1-b)-quinazolin-2-(1H)-one, H₂O

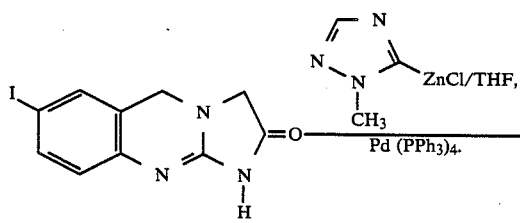

n-Butyl lithium (6.6 cm³ of a 1.6M solution in n-hexane) was added to a stirred solution of 1-methyl-1,2,4-triazole (0.83 g) in THF (20 cm³) at −70° under nitrogen. After stirring for 1 hour at −70° the white syspension was treated with a solution of anhydrous zinc chloride (4.1 g) in THF (20 cm³) and the mixture was warmed to room temperatue. 7-Iodo-1,2,3,5-tetrahydroimidazo(2,1-b)quinazolin-2-(1H)-one (1.33 g) and tetrakis (triphenylphosphine)palladium (O) (0.05 g) were added and the mixture was heated under reflux for 6 hours. The cooled solution was evaporated in vacuo and the residue partitioned between dichloromethane:methanol, 9:1 (200 cm³), and a solution of ethylenediaminetetraacetic acid disodium salt (10 g) in water (200 cm³). The aqueous phase was further extracted with dichloromethane:methanol, 9:1 (2×150 cm³), and the combined and dried (MgSO₄) organic phases were evaporated in vacuo to give a solid which was chromatographed on silica (Merck "MK 60.9385" [Trade Mark]) eluting with chloroform:methanol:aqueous ammonia (S.G. 0.880), 90:10:1. Combination and evaporation of appropriate fractions afforded a solid (0.36 g) which was recrystallised from chloroform-methanol to give the title compound, m.p. 340°-343° (0.16 g).

Analysis %: Found: C,54.7; H,4.3; N,28.9; Calculated for $C_{13}H_{12}N_6O.H_2O$: C,54.5; H,4.9; N,29.4.

EXAMPLES 5 and 6

The following compounds were prepared similarly to the previous Example starting from the appropriately substituted 7-iodo-1,2,3,5-tetrahydroimidazo(2,1-b)quinazolin-2-(1H)-one, 1-methyl-1,2,4-triazol-5-yl zinc chloride and tetrakis (triphenylphosphine) palladium (O).

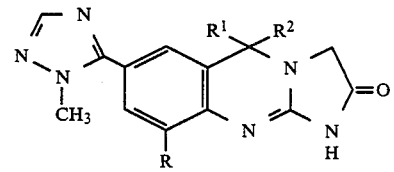

| Example No. | R | R¹ | R² | Form Isolated and m.p. (°C.) | Analysis % (Theoretical in brackets) | | |
|---|---|---|---|---|---|---|---|
| | | | | | C | H | N |
| 5 | —CH₃ | —H | —H | Free base, 0.5 H₂O, 215° | 57.4 (57.7 | 4.7 5.2 | 28.8 28.8) |
| 6 | —H | —CH₃ | —H | Free base, monohydrate, 285° | 56.0 (56.0 | 5.0 4.7 | 28.0 28.0) |

EXAMPLE 7

7-(2,4-Dimethylimidazol-1-yl)-1,2,3,5-tetrahydroimidazo-(2,1-b)-quinazolin-2-(1H)-one, 1.75 H₂O

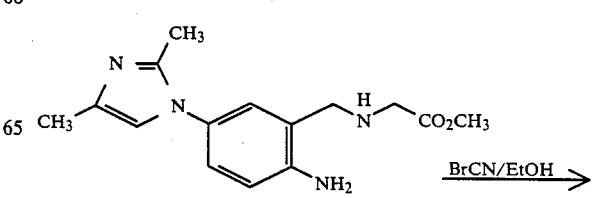

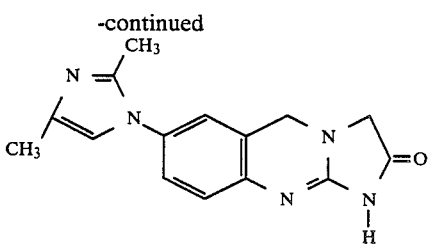

A mixture of methyl N-(2-amino-5-[2,4-dimethylimidazol-1-yl]benzyl)glycinate (0.41 g) and cyanogen bromide (0.159 g) was heated under reflux in ethanol (5 cm³) for 72 hours. On cooling to room temperature a precipitate formed and the resulting suspension was treated with a solution of sodium hydroxide (0.06 g) in water (3 cm³). The solid material dissolved and after 2 hours at room temperature a solid precipitated which was filtered off and washed with ethanol (5 cm³) to afford the title compound, m.p. 324°–328° (0.19 g).

Analysis %: Found: C,57.6; H,5.0; N,22.4; Calculated for $C_{15}H_{15}N_5O$, 1.75 $H_2O$: C,57.6; H,6.0; N,22.4.

EXAMPLES 8 and 9

The following compounds were prepared similarly to the previous Example starting from the appropriately substituted methyl N-benzylglycinate derivative (Example 8) or ethyl N-benzylglycinate derivative (Example 9) together with cyanogen bromide in refluxing ethanol, followed by treatment with aqueous sodium hydroxide at room temperature:

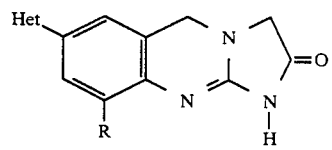

| Example No. | Het | R | Form Isolated and m.p. (°C.) | Analysis % (Theoretical in brackets) C | H | N |
|---|---|---|---|---|---|---|
| 8 | (imidazol) | —H | Free base 0.5 $H_2O$, >340°. | 54.6 (54.7 | 3.9 4.2 | 31.9 31.9) |
| 9 | (imidazol) | —CH₃ | Free base, 318–319.5° | 54.8 (54.5 | 4.7 4.9 | 29.6 29.4) |

EXAMPLE 10

7-(2,4-Dimethylimidazol-1-yl)-9-methyl-1,2,3,5-tetrahydroimidazo-(2,1-b)quinazolin-2-(1H)-one

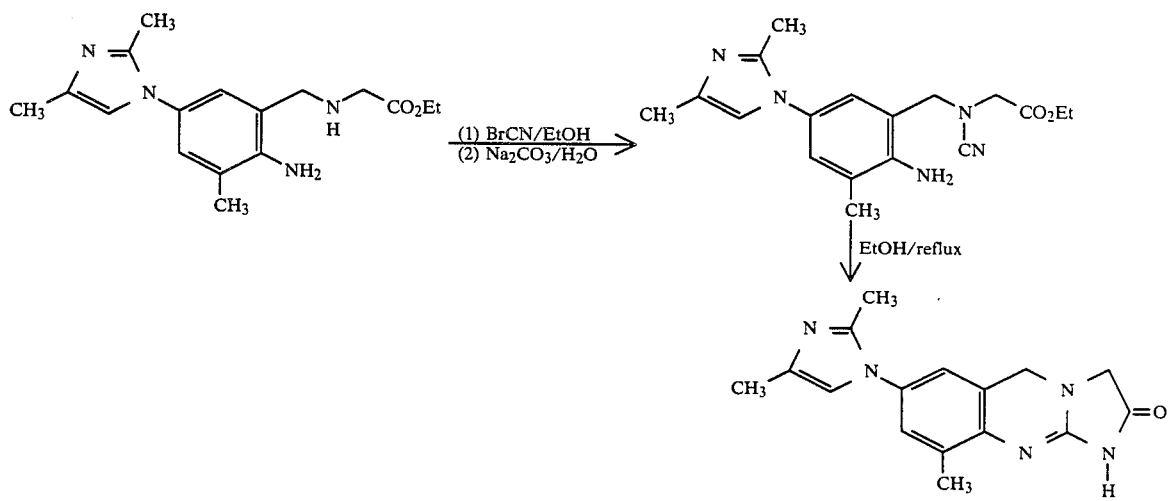

A mixture of ethyl N-(2-amino-3-methyl-5-[2,4-dimethylimidazol-1-yl]benzyl)glycinate (0.75 g) and cyanogen bromide (0.265 g) was stirred in ethanol (5 cm³) for 1 hour. The mixture was partitioned between dichloromethane (25 cm³) and 10% aqueous sodium carbonate solution (10 cm³) and the aqueous phase was further extracted with dichloromethane (2×10 cm³). The combined and dried (MgSO₄) organic extracts were evaporated in vacuo, and the residue chromatographed on silica (Merck "MK 60.9385" [Trade Mark]), eluting with dichloromethane:methanol, 19:1. Combination and evaporation of the appropriate fraction gave a solid (0.6 g), a small portion of which was recrystallised from ethyl acetate-methanol to afford ethyl N-cyano-N-(2-amino-3-methyl-5-[2,4-dimethylimidazol-1-yl]benzyl)-glycinate, m.p. 135°–140°. The remaining material was heated under reflux in ethanol (5 cm³) for 24 hours, the solvent was removed in vacuo, and the residue was chromatographed on silica (Merck "MK 60.9385" [Trade Mark]), eluting with dichloromethane:methanol, 19:1. Combination and evaporation of the appropriate fractions gave a solid which was recrystallised from ethyl acetate-methanol to afford the title compound, m.p. 310°–312° C. (0.28 g).

Analysis %: Found: C,64.8; H,5.8; N,23.6; Calculated for $C_{16}H_{17}N_5O$: C,65.1; H,5.8; N,23.7.

EXAMPLES 11–14

The following compounds were prepared similarly to the previous Example starting from the appropriately substituted ethyl N-benzylglycinate derivative (Examples 11, 13 and 14) or methyl N-benzylglycinate derivative (Example 12), together with cyanogen bromide in ethanol. [The intermediate N-cyano derivatives were isolated in crude form in all cases, being cyclised directly without purification and characterisation.]

hour volatile material was removed in vacuo and the residue was partitioned between chloroform (200 -cm³) and saturated aqueous sodium carbonate solution (50 cm³). The aqueous phase was further extracted with chloroform (2×50 cm³) and the combined organic extracts were washed with 10% aqueous sodium thiosulphate solution (50 cm³). The dried (MgSO₄) organic extracts were evaporated in vacuo and the oily residue was chromatographed on silica (Merck "MK 60.9385" [Trade Mark]) eluting with chloroform. Combination and evaporation of the appropriate fractions gave a solid (4.9 g), a small portion of which was recrystallised

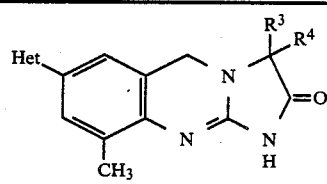

| Example No. | Het | $R^3$ | $R^4$ | Form Isolated and m.p. (°C.) | Analysis % (Theoretical in brackets) | | |
|---|---|---|---|---|---|---|---|
| | | | | | C | H | N |
| 11 | CH₃–C(=N–)–N(CH₃)–N= (pyrazole with CH₃) | —CH₃ | —H | Free base 0.5 H₂O, 263–266°. | 64.3 (64.1 | 6.2 6.3 | 21.9 22.0) |
| 12* | CH₃–C(=N–)–N(CH₃)–N= | —CH₃ | —CH₃ | Free base H₂O, 230–233°. | 63.1 (63.3 | 6.4 6.8 | 20.2 20.5) |
| 13 | N=C–N–N= (triazole) | —H | —H | Free base H₂O, >360° | 54.1 (54.5 | 4.7 4.9 | 28.9 29.4) |
| 14 | HO–pyridyl–N | —H | —H | Free base 0.75 C₂H₅OH, >350° | 63.9 (63.9 | 5.5 5.6 | 17.2 17.1) |

*The cyclisation of the intermediate N—cyano derivative to the required tricyclic compound was carried out in this case in n-butanol under reflux for 16 hours.

The following Preparations illustrate the synthesis of the novel starting materials used in the preceding Examples. All temperatures are in °C.:

Preparation 1

Ethyl N-(2-Amino-5-iodobenzyl)glycinate

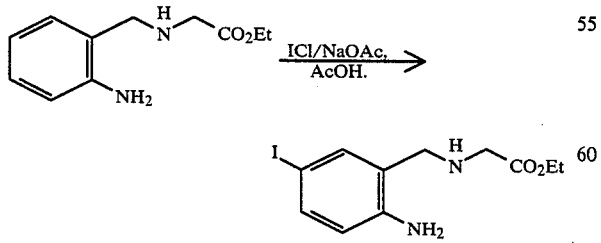

Iodine monochloride (3.24 g) was added to a stirred solution of ethyl N-(2-aminobenzyl)glycinate (4.16 g) (see U.S. Pat. No. 3,983,120) and sodium acetate (1.804 g) in acetic acid (100 cm³) at room temperature. After 1 from hexane-ethyl acetate to afford the title compound, m.p. 58°–61°.

Analysis %: Found: C,39.5; H,4.5; N,8.4; Calculated for $C_{11}H_{15}IN_2O_2$: C,39.5; H,4.5: N,8.4.

Preparations 2 and 3

The following compounds were prepared similarly to Preparation 1 starting from the appropriately substituted ethyl N-(2-aminobenzyl)glycinate, sodium acetate, acetic acid, and iodine monochloride:

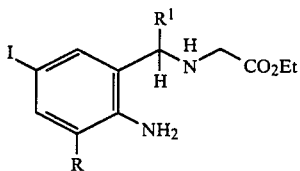

| Preparation No. | R | R¹ | Form Isolated and m.p. (°C.) | Analysis % (Theoretical in brackets) | | |
|---|---|---|---|---|---|---|
| | | | | C | H | N |
| 2 | —CH₃ | —H | Free base, 64–67° | 41.9 (41.4 | 4.9 4.9 | 8.1 8.1) |
| 3 | —H | —CH₃ | Free base, oil. | 41.2 (41.4 | 4.9 4.9 | 7.9 8.1) |

The ester starting material used in Preparation 3 is a known compound (see U.S. Pat. No. 3,932,407).

The starting material used in Preparation 2 was prepared similarly to the method of Preparation 11 using 2-amino-3-methylbenzaldehyde and ethyl glycinate, followed by hydrogenation over Pd-C.

Preparation 4

7-Iodo-1,2,3,5-tetrahydroimidazo(2,1-b-quinazolin-2-(1H)-one

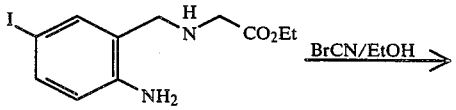

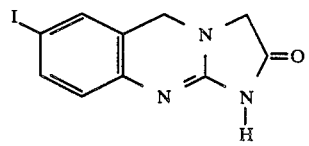

A mixture of ethyl N-(2-amino-5-iodobenzyl)glycinate (3.34 g) and cyanogen bromide (1.11 g) was heated under reflux in ethanol (20 cm³) for 18 hours. A solution of sodium hydroxide (0.42 g) in water (5 cm³) was added to the cooled (room temperature) solution and the mixture was stirred for a further 2 hours. The mixture was then filtered and the solid was washed with water (10 cm³) and dried in vacuo. A small portion of this material was chromatographed on silica (Merck MK "60.9385" [Trade Mark]) eluting with chloroform-:methanol, 19:1. Combination and evaporation of the appropriate fractions afforded a solid which was triturated with isopropanol to give the title compound, m.p. 323°–324°.

Analysis %: Found: C,38.3; H,2.7; N,13.2; Calculated for C₁₀H₈IN₃O: C 38.4; H,2.6; N,13.4.

Preparations 5 and 6

The following compounds were prepared similarly to the previous Preparation using the appropriately substituted ethyl N-(2-amino-5-iodobenzyl)glycinate and cyanogen bromide as the starting materials:

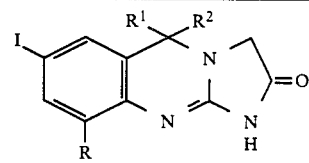

| Preparation No. | R | R¹ | R² | Form Isolated and m.p. (°C.) | Analysis % (Theoretical in brackets) | | |
|---|---|---|---|---|---|---|---|
| | | | | | C | H | N |
| 5 | —CH₃ | —H | —H | Free base, 280° | 40.8 (40.4 | 3.2 3.1 | 12.5 12.8) |
| 6 | —H | —CH₃ | —H | Free base, 289–90° | 40.7 (40.4 | 3.2 3.1 | 12.7 12.8) |

Preparation 7

2-Amino-5-iodo-3-methylbenzoic acid

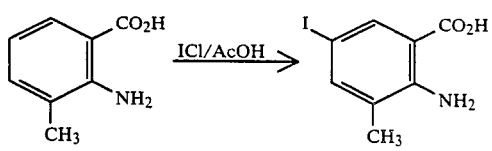

Iodine monochloride (28.9 g) was added over 0.5 hours to a stirred solution of 2-amino-3-methylbenzoic acid (24.5 g) (Aldrich Chemical Co. Ltd.) in acetic acid (250 cm³). After 24 hours ether (250 cm³) was added and the mixture was filtered. The solid material was dried in vacuo to afford the title compound, m.p. 214° (38.6 g).

Analysis %: Found: C,35.1; H,2.9; N,5.2; Calculated for C₈H₈INO₂: C,34.7; H,2,9; N,5.1.

Preparation 8

2-Amino-5-iodo-3-methylbenzyl alcohol

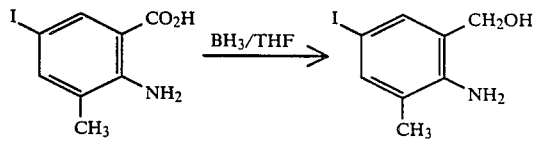

A solution of borane in THF (270 cm³ of a 1M solution) was added over 0.5 hours to a stirred suspension of 2-amino-5-iodo-3-methylbenzoic acid (18.48 g) in THF (400 cm³) at 0°. After stirring at 0° for 0.5 hours, the reaction mixture was warmed to 50° for a further 3 hours. After cooling in an ice-bath, water (25 cm³) was cautiously added dropwise with stirring, the resulting mixture was treated with an aqueous 10% solution of sodium hydroxide (100 cm³), and stirring was continued for a further 24 hours. Volatile material was then removed in vacuo and the residue was partitioned between water (100 cm³) and chloroform (200 cm³). The aqueous phase was re-extracted with chloroform (2×200 cm³), and the combined and dried (MgSO₄) organic extracts were evaporated in vacuo to give an oil which was chromatographed on silica (Merck "MK 60.9385" [Trade Mark]) eluting with chloroform. Combination and evaporation of appropriate fractions afforded the title compound, m.p. 101°–103° (14.22 g).

Analysis%: Found: C,36.7; H,4.0; N,5.4; Calculated for C$_8$H$_{10}$NOI: C,36.5; H,3.8; N,5.3.

Preparation 9

2-Amino-5-iodo-3-methylbenzaldehyde

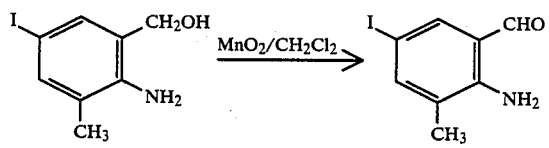

Freshly dried manganese dioxide (3.3 g) was added to a solution of 2-amino-5-iodo-3-methylbenzyl alcohol (2.0 g) in dichloromethane (50 cm$^3$) under nitrogen and the mixture was stirred for 3 days at room temperature. The mixture was filtered, the filtrate evaporated to dryness, and the solid residue was chromatographed on silica (Merck "MK 60.9385" [Trade Mark]) eluting with dichloromethane. Combination and evaporation of appropriate fractions afforded the title compound, m.p. 134° (1.6 g).

Analysis %: Found: C,37.2; H,3.2; N,5.4 Calculated for C$_8$H$_8$INO: C,36.8; H,3.1; N,5.4.

Preparation 10

(Alternative route to Preparation 2)

Ethyl N-(2-amino-5-iodo-3-methylbenzyl)glycinate

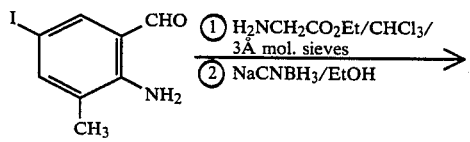

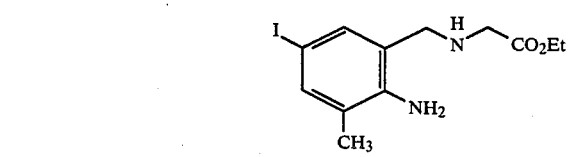

A mixture of freshly prepared ethyl glycinate (2.58 g), 2-amino-5-iodo-3-methylbenzaldehyde (4.03 g) and 3Å molecular sieves (2 g "Fluka A.G." [Trade Mark] article No. 69828) was heated with stirring under reflux in chloroform (50 cm$^3$) for 4 hours. The cooled solution was filtered, evaporated in vacuo, and the residue taken into ethanol (30 cm$^3$) and treated with sodium cyanoborohydride (1.43 g). After stirring for 72 hours ethanol was removed in vacuo and the residue was partitioned between chloroform (50 cm$^3$) and aqueous ammonia (50 cm$^3$, S.G. 0.88). The aqueous phase was further extracted with chloroform (2×100 cm$^3$) and the combined organic extracts were dried (MgSO$_4$) and evaporated to give the title compound as a crude oil, (2.5 g).

Preparation 11

Ethyl N-(2-amino-3-methyl-5-[1,2,4-triazol-1-yl]benzyl)glycinate

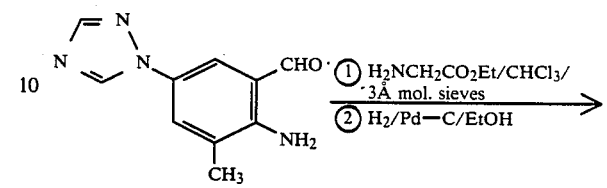

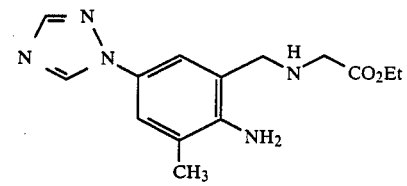

A mixture of ethyl glycinate (0.38 g), 1-(4-amino-3-formyl-5-methylphenyl)-1,2,4-triazole (0.5 g) and 3Å molecular sieves (1.0 g; "Fluka" [Trade Mark] article No. 69828) was stirred and heated under reflux in chloroform (10 cm$^3$) for 4 hours. The cooled mixture was filtered, evaporated in vacuo, and the residue taken into ethanol (30 cm$^3$). The solution was then hydrogenated at 60 p.s.i. (4.13×10$^5$ Pa) pressure and room temperature (20°) over 10% palladised charcoal (0.2 g) for 16 hours. The catalyst was then removed by filtration through "Solkafloc" (Trade Mark) and the solution was evaporated in vacuo to give an oil which was chromatographed on silica (Merck "MK 60.9385" [Trade Mark]) eluting with chloroform. Combination and evaporation of the appropriate fractions afforded the title compound as an oil (0.37 g).

Preparation 12

Ethyl N-(5-fluoro-2-nitrobenzyl)glycinate

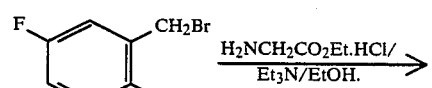

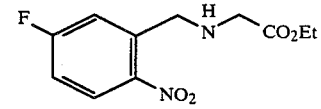

A mixture of ethyl glycinate monohydrochloride (4.18 g) and triethylamine (5.6 cm$^3$) in ethanol (40 cm$^3$) was heated until all the solid material was consumed. A solution of 3-fluoro-6-nitrobenzylbromide (2.34 g) in ethanol (20 cm$^3$) was then added dropwise over 0.5 hours at reflux, followed by further heating for 1 hour. The cooled mixture was evaporated in vacuo and the residue partitioned between dichloromethane (100 cm$^3$) and saturated aqueous sodium carbonate solution (50 cm$^3$). The aqueous phase was further extracted with dichloromethane (2×50 cm$^3$) and the combined and dried (MgSO$_4$) organic extracts were evaporated in vacuo to give an oil which was chromatogrpahed on silica (Merck "MK 60.9385" [Trade Mark]), eluting with chloroform. Combination and evaporation of the appropriate fractions afforded the title compound as an oil (1.15 g), used directly.

3-Fluoro-6-nitrobenzylbromide is a known compound.

Preparation 13

Ethyl N-trifluoroacetyl-N-(5-fluoro-2-nitrobenzyl)-glycinate

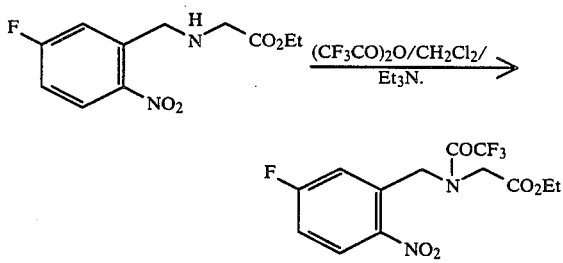

Trifluoroacetic anhydride (3.0 cm$^3$) was added dropwise to a stirred solution of ethyl N-(3-fluoro-6-nitrobenzyl)glycinate (5.10 g) and triethylamine (3.0 cm$^3$) in dichloromethane (40 cm$^3$) at $-70°$ under nitrogen. The mixture was warmed to room temperature and partitioned between dichloromethane (60 cm$^3$) and 10% sodium carbonate solution (50 cm$^3$). The organic phase was dried (MgSO$_4$), evaporated in vacuo, and the oily residue was chromatographed on silica (Merck "MK 60.9385" [Trade mark]) eluting with ethyl acetate:hexane, 1:9. Combination and evaporation of the appropriate fractions gave an oil (6.27 g) which crystallised on standing for several days to afford the title compound, m.p. 60°–63°.

Analysis %: Found: C,44.2; H,3.4; N,8.1; Calculated for C$_{13}$H$_{12}$F$_4$N$_2$O$_5$: C,44.3; H,3.4; N,8.0.

Preparation 14

Ethyl N-trifluoroacetyl-N-(2-nitro-5-[2,4-dimethylimidazol-1-yl]benzyl)glycinate

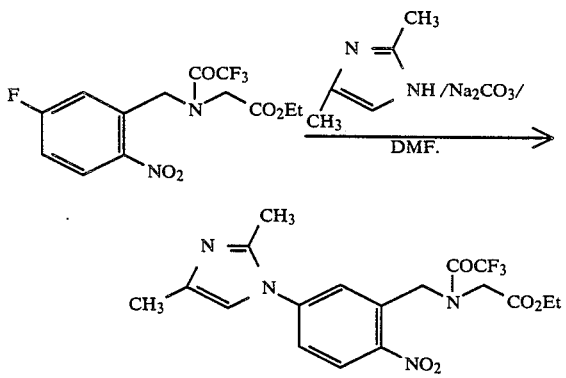

A mixture of 2,4-dimethylimidazole (6.25 g), ethyl N-trifluoroacetyl-N-(5-fluoro-2-nitrobenzyl)glycinate (22.0 g) and sodium carbonate (6.62 g) was stirred and heated at 130° for 2 hours. Volatile material was removed from the cooled mixture in vacuo and the residue was partitioned between ethyl acetate (200 cm$^3$) and water (100 cm$^3$). The organic phase was washed with water (2×25 cm$^3$), dried (MgSO$_4$), and evaporated in vacuo to give an oil which was chromatographed on silica (Merck "MK 60.9385" [Trade Mark]) eluting with ethyl acetate:methanol, 1:19. Combination and evaporation of the appropriate fractions gave an oil which crystallised on trituration with ether to afford the title compound, m.p. 172.5°–176° (3.1 g). Analysis %: Found: C,50.7; H,4.8; N,12.7; Calculated for C$_{18}$H$_{19}$F$_3$N$_4$O$_5$: C,50.5; H,4.5; N,13.1.

Ethyl N-trifluoroacetyl-N-(2-nitro-5-[1,2,4-triazol-1-yl]benzyl)glycinate, m.p.

Preparation 15 99°–102°, was prepared similarly to the previous Preparation using N-trifluoroacetyl-N-(5-fluoro-2-nitrobenzyl)glycinate and 1,2,4-triazole as the starting materials.

Analysis %: Found: C,44.7; H,3.5; N,17.4; Calculated for C$_{15}$H$_{14}$F$_3$N$_5$O$_5$: C,44.9; H,3.5; N,17.4.

Preparation 16

Ethyl N-trifluoroacetyl-N-(2-amino-5-[2,4-dimethylimidazol-1-yl]benzyl)glycinate, 0.25 H$_2$O

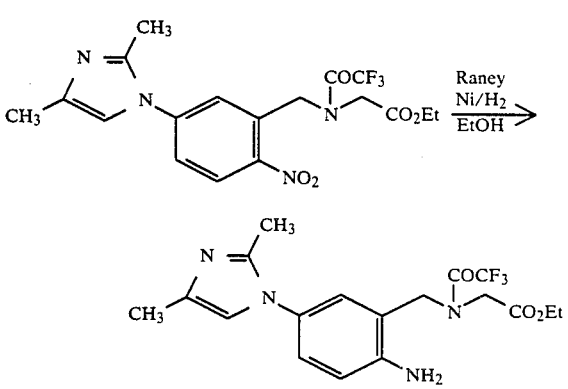

A solution of ethyl N-trifluoroacetyl-N-(2-nitro-5-[2,4-dimethylimidazol-1-yl]benzyl)glycinate (1.5 g) in ethanol (60 cm$^3$) was hydrogenated at room temperature and 20 p.s.i. (1.38×10$^5$ Pa) hydrogen pressure over Raney nickle (0.15 g) for 3 hours. The mixture was filtered through "Solkafloc" (Trade Mark), and evaporated in vacuo to give an oil (1.4 g) which crystallised on trituration with ether to afford the title compound, m.p. 163°–166°.

Analysis %: Found: C,53.4; H,5.1; N,13.7; Calculated for C$_{18}$H$_{21}$F$_3$N$_4$O$_3$.0.25 H$_2$O: C,53.7; H,5.4; N,13.9.

Preparation 17

Ethyl N-trifluoroacetyl-N-(2-amino-5-[1,2,4-triazol-1-yl]benzyl)glycinate, crude oil, was prepared similarly to the previous Preparation using ethyl N-trifluoroacetyl-N-(2-nitro-5-[1,2,4-triazol-1-yl]benzyl)glycinate as the starting material.

Preparation 18

Methyl N-(2-amino-5-[2,4-dimethylimidazol-1-yl]benzyl)glycinate

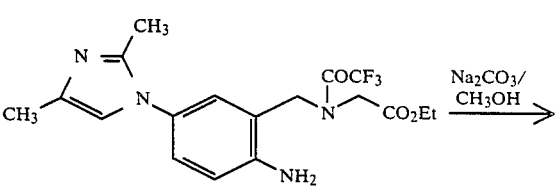

-continued

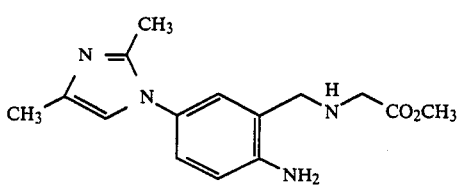

A mixture of ethyl N-trifluoroacetyl-N-(2-amino-5-[2,4-dimethylimidazol-1-yl]benzyl)glycinate (1.4 g) and anhydrous sodium carbonate (0.74 g) in methanol (20 cm³) was heated under reflux for 3 hours. The cooled solution was evaporaed to dryness in vacuo and the residue was partitioned between chloroform (50 cm³) and water (10 cm³). The aqueous phase was re-extracted with chloroform (2×25 cm³) and the combined and dried (MgSO₄) organic extracts were evaporated to give an oil which was chromatographed on silica (Merck "MK 60.9385" [Trade mark]), eluting with ethyl acetate:methanol, 9:1. Combination and evaporation of the appropriate fractions afforded the title compound as an oil (0.41 g), used directly.

Preparation 19

Methyl N-(2-amino-5-[1,2,4-triazol-1-yl]benzyl)glycinate, crude oil, was prepared similarly to the previous Preparation using ethyl N-trifluoroacetyl-N-(2-amino-5-[1,2,4-triazol-1-yl]benzyl)glycinate and sodium carbonate in methanol as the starting materials.

Preparation 20

1-(4Amino-3-formyl-5-methylphenyl)-1,2,4-triazole

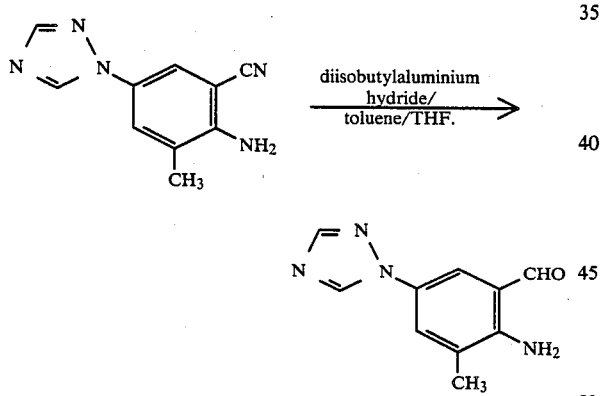

Diisobutylalumnium hydride (11.1 cm³ of a 1.5M solution in toluene) was added dropwise at 0° to a stirred suspension of 1-(4-amino-3-cyano-5-methylphenyl)-1,2,4-triazole (15 g) in THF (20 cm³). The solution was stirred at room temperature for 0.5 hours, heated under reflux for 2 hours, cooled, and treated with methanol (1 cm³) and water (100 cm³). Solid material was filtered off and washed with methanol (50 cm³) and the filtrate was evaporated in vacuo. The residue was taken into 2M hydrochloric acid (20 cm³), warmed for 10 minutes at 100°, and cooled. The solution was neutralised with saturated aqueous sodium carbonate solution and extracted with chloroform (4×50 cm³). The combined organic extracts were dried (MgSO₄) and evaporated to give an oil which was chromatographed on silica (Merck "MK 60.9385" [Trade Mark]) eluting with ethyl acetate. Combination and evaporation of appropriate fractions followed by recrystallisation from ethyl acetate/hexan afforded the title compound, m.p. 209°–211° (1.27 g), characterised by n.m.r. and i.r. spectroscopy.

Preparation 21

1-(4-Amino-3-cyano-5 methylphenyl)-1,2,4-triazole

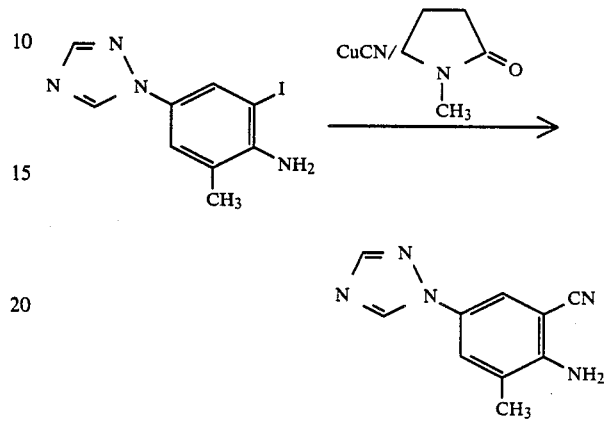

A mixture of 1-(4-amino-3-iodo-5-methyl-phenyl)-1,2,4-triazole (14.23 g) and cuprous cyanide (5.94 g) was heated at 120° in N-methylpyrrolidone (32 cm³) for 2.5 hours. The cooled mixture was poured into ammonia solution (100 cm³; S.G. 0.880) and the resulting solution was extracted with chloroform:methanol, 19:1 (3×150 cm³). The combined and dried (MgSO₄) organic extracts were filtered and evaporated in vacuo (0.5 mm) to afford an oil which was chromatographed on silica (Merck "MK 60.9385" [Trade Mark]) eluting with ethyl acetate:methanol, 19:1. Combination and evaporation of appropriate fractions gave an oil which crystallised on trituration with ether to give the title compound, m.p. 231°–3° (2.8 g).

Analysis %: Found: C,59.8; H,4.6; N,35 6; Calculated for $C_{13}H_{14}N_4 \cdot 1/3$ $H_2O$: C,60.3; H,4.6; N,35.2.

Preparation 22

1-(4-Amino-3-iodo-5 methylphenyl)-1,2,4-triazole

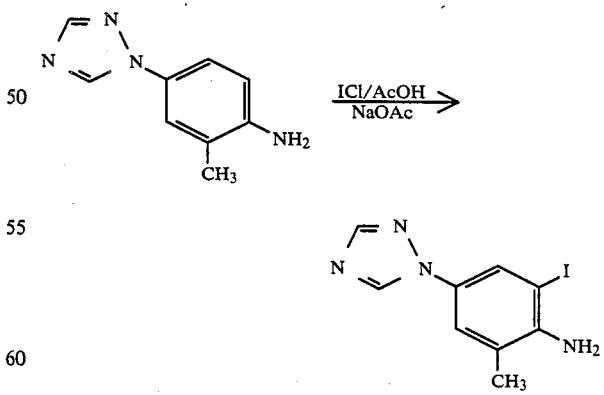

Iodine monochloride (5.103 g) was added dropwise to a stirred solution of 1-(4-amino-3-methylphenyl)-1,2,4-triazole (5.22 g) and sodium acetate (2.583 g) in acetic acid (100 cm³). After 16 hours volatile material was removed in vacuo and the residue was partitioned between dichloromethane (100 cm³) and sodium carbonate solution (50 cm³). The organic phase was washed with sodium thiosulphate solution (10 g in 50 cm³ water), dried (MgSO₄) and evaporated to give a solid which was chromatographed on silica (Merck "MK 60.9385" [Trade Mark]) eluting with ethyl acetate. Combination and evaporaton of the appropriate fractions gave a solid which was recrystallised from ethyl acetate-ether to afford the title compound, m.p. 151°–154° (3.1 g).

Analysis %: Found: C,36.6; H,3.1; N,19.0; Calculated for $C_9H_9IN_4$: C,36.0; H,3.0; N,18.7.

Preparation 23

1-(4-Amino-3-methylphenyl)-1,2,4-triazole

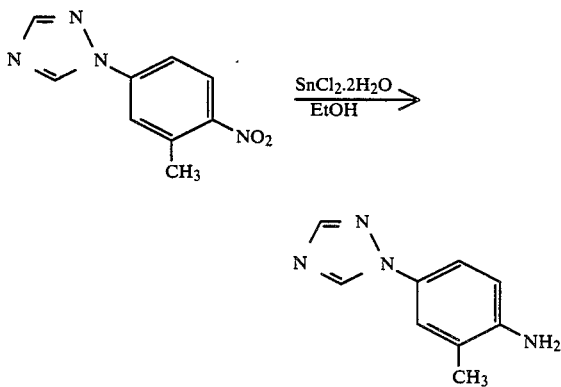

Stannous chloride dihydrate (225 g) was added portionwise to a stirred suspension of 1-(3-methyl-4-nitrophenyl)-1,2,4-triazole (42 g) in absolute ethanol (500 cm³). After heating under reflux for 4 hours, the cooled mixture was basified to pH8 with aqueous 2.5M sodium hydroxide and filtered. The filtrate was evaporated in vacuo, partitioned between chloroform (200 cm³) and water (50 cm³), and the aqueous phase was further extracted with chloroform (2×100 cm³). The combined and dried (MgSO₄) organic extracts were concentrated in vacuo to give a solid (30 g) which was recrystallised from ethyl acetate to afford 1-(4-amino-3-methylphenyl)-1,2,4-triazole m.p. 122°–5°.

Analysis %: Found: C,61.9; H,5.9; N,32.1; Calculated for $C_9H_{10}N_4$: C,62.1; H,5.8; N,32.2.

Preparation 24

1-(3-Methyl-4-nitrophenyl)-1,2,4-triazole

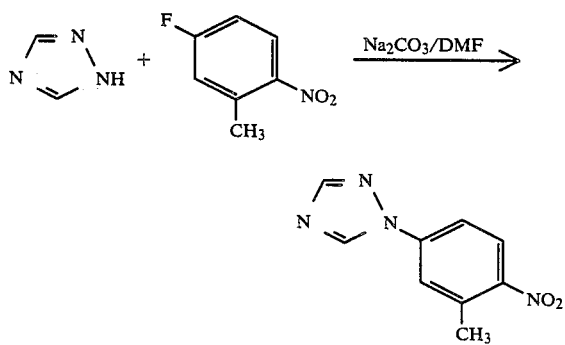

A mixture of 3-fluoro-6-nitrotoluene (50.0 g), 1,2,4-triazole (22.2 g) and sodium carbonate (34.0 g) was heated with stirring in dimethylformamide (300 cm³) at 130° for 16 hours. The cooled mixture was then concentrated in vacuo, the residue was acidified to pH1 with 4M hydrochloric acid, and the resulting solution was extracted with chloroform (2×25 cm³) to remove any neutral material. The combined aqueous phases were basified to pH10 with 2.5M sodium hydroxide solution and the mixture was extracted with chloroform (3×250 cm³). The combined and dried (MgSO₄) organic extracts were concentrated in vacuo to give a solid which was recrystallised from toluene to give 1-(3-methyl-4-nitrophenyl)-1,2,4-triazole, m.p. 116°–7°.

Analysis %: Found: C,52.9; H,3.9; N,27.6 Calculated for $C_9H_8N_4O_2$: C,52.9; H,3.9; N,27.5.

Preparation 25

Ethyl N-(2-amino-3-methyl-5-[2,4-dimethylimidazol-1-yl]benzyl)-glycinate

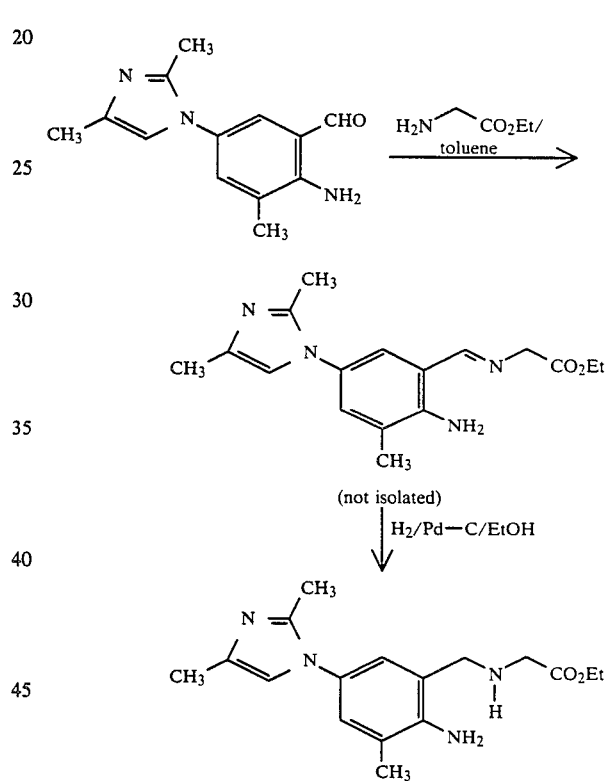

A mixture of ethyl glycinate (2.2 g) and 1-(4-amino-3-formyl-5-methylphenyl)-2,4-dimethylimidazole (0.647 g) was heated under reflux in toluene (30 cm³) for 3 hours, with constant removal of water using a Dean and Stark apparatus. Volatile material was removed in vacuo to give the intermediate imine as a crude oil (0.84 g). This material was not purified but was taken directly into absolute ethanol (25 cm³) and hydrogenated at 25° and 60 p.s.i. pressure over 10% palladised charcoal (0.1 g) for 2.5 hours. The mixture was filtered through "Solkafloc" (Trademark) and the ethanol was removed in vacuo to afford the title compound as an oil (75 g).

Preparations 26 and 27

The following compounds were prepared similarly to Preparation 25 using either racemic alaine ethyl ester (Preparation 26) or methyl-2aminoisobutyrate (Preparation 27), 1-(4-amino-3-formyl-5-methylphenyl)-2,4- dimethylimidazole, and hydrogen over Pd/C as the starting meterials:

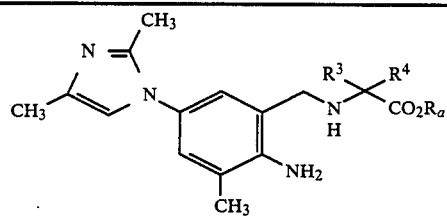

| Preparation No. | R³ | R⁴ | R_a | Form Isolated |
|---|---|---|---|---|
| 26 | —CH₃ | —H | —CH₂CH₃ | Free base, crude oil |
| 27* | —CH₃ | —CH₃ | —CH₃ | Free base, crude oil |

*In this case the formation of the intermediate imine took 16 hours in refluxing toluene and the subsequent hydrogenation step took 48 hours.

Preparation 28

Ethyl N-(2-amino-3-methyl-5-[1,2,4-triazol-4-yl]benzl)glycinate

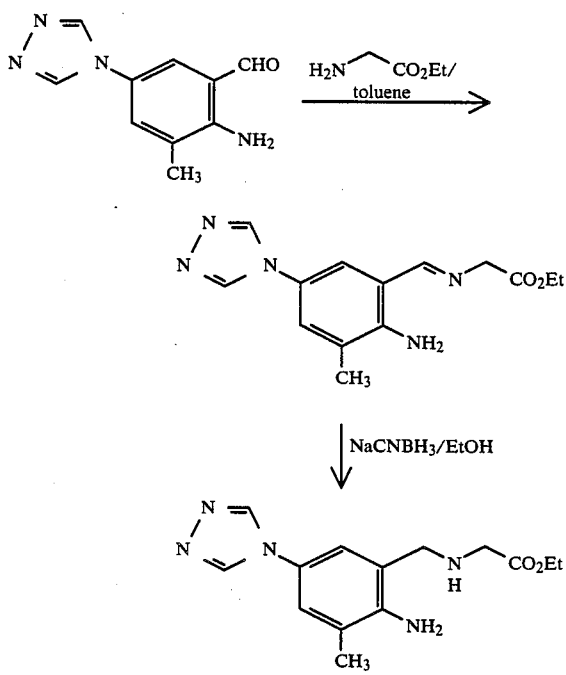

A mixture of ethyl glycinate (5.7 g) and 4-(4-amino-3-formyl-5-methylphenyl)-1,2,4-triazole (1.62 g) was treated under reflux in toluene (120 cm³) for 2.5 hours, with constant removal of water using a Dean and Stark apparatus. Volatile material was removed in vacuo to give the intermediate imine as a crude solid (2.35 g). This material was not purified but was taken directly into absolute ethanol (200 cm³) and treated with sodium cyanoboro-hydride (5.0 g). After heating under reflux for 10 hours, the cooled solution was evaporated in vacuo to ca. 50 cm³ volume and poured onto 2% aqueous sodium carbonate solution (100 cm³). The mixture was extracted with dichloromethane (3×200 cm³) and the combined and dried (MgSO₄) organic extracts were evaporated in vacuo to give an oil which was chromatographed on silica (Merck "MK 60.9385 [Trade Mark]) eluting with dichloromethane:ethanol, 19:1. Combination and evaporation of the appropriate fractions afforded the title compound as an oil (1.14 g).

Preparation 29

1-(4-Amino-3-formyl-5-methylphenyl)-2,4-dimethylimidazole.0.5 H₂O

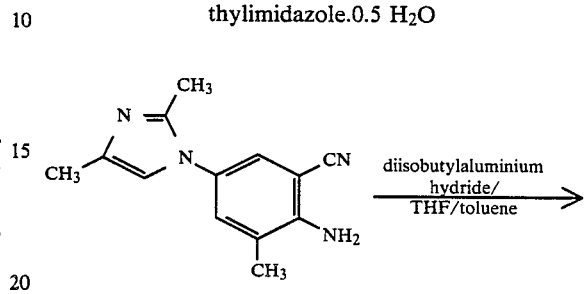

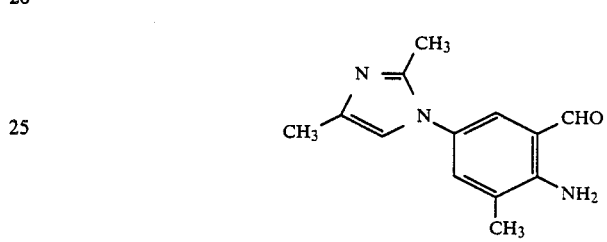

A stirred suspension of 1-(4-amino-3-cyano-5-methylphenyl)-2,4-dimethylimidazole (2.26 g) in tetrahydrofuran (THF) (30 cm³) was cooled to 0° and treated dropwise with a solution of diisobutylaluminium hydride (17 cm³ of a 1.5M solution in toluene). The mixture was then warmed to 55° for one hour, cooled to 0° and cautiously treated with methanol (5 cm³). After dilution with water (20 cm³) the precipitated aluminium salts were removed by filtration and the filtrate was treated with 2M hydrochloric acid (20 cm³). The aqueous solution was then basified with saturated aqueous sodium carbonate solution (pH 9) and the mixture was extracted with dichloromethane (4×20 cm³). The combined and dried (MgSO₄) organic extracts were evaporated in vacuo to give an oil which was chromatographed on silica (Merck "MK 60.9385" [Trade Mark]), eluting with dichloromethane:methanol, 19:1. Combination and evaporation of the appropriate fractions gave a solid which was recrystallised from ethyl acetate to afford the title compound, m.p. 203°–207° (1.2 g).

Analysis %: Found: C,65.3; H,6.4; N,18.2; Calculated for $C_{13}H_{15}N_3.0.5\ H_2O$: C,65.2; H,6.8; N,17.6.

Preparation 30

4-(4-Amino-3-formyl-5-methylphenyl)-1,2,4-triazole, m.p. 250°–252°, was prepared similarly to the previous Preparation, using 4-(4-amino-3-cyano-5-methylphenyl)-1,2,4-triazole and diisobutylaluminium hydride as the starting materials.

Analysis %: Found: C,59.3; H,5.1; N,28.0; Calculated for $C_{10}H_{10}N_4O$: C,59.4; H,5.0; N,27.7.

Preparation 31 (alternative to Preparation 30)

4-(4-Amino-3-formyl-5-methylphenyl)-1,2,4-triazole

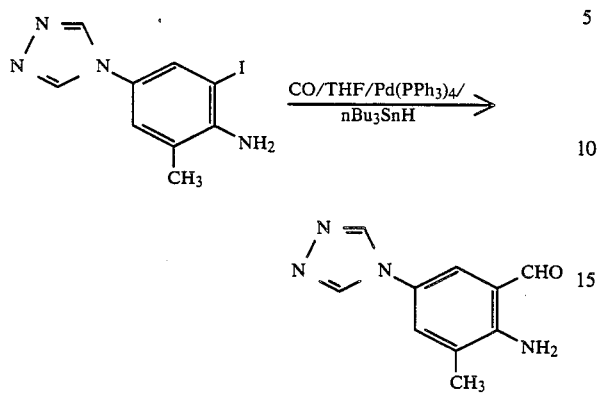

A stirred mixture of 4-(4-amino-3-iodo-5-methylphenyl)-1,2,4-triazole (3.0 g) and tetrakis (triphenylphosphine) palladium (0) (1.0 g) in THF (300 cm³) was deoxygenated with a stream of nitrogen for 0.5 hours. The mixture was then placed under carbon monoxide (ca 2 atmospheres pressure), warmed to 50°, and a solution of tri-n-butyltin hydride (3.2 g) in THF (200 cm³) was added dropwise over 4 hours. After a further 0.5 hours, the mixture was poured onto an aqueous solution of potassium fluoride (10 g) in water (200 cm³) and the mixture was extracted with dichloromethane (5×200 cm³). The combined and dried (MgSO₄) extracts were evaporated in vacuo and the residue was chromatographed on silica (Merck "MK 60.9385" [Trade Mark]), eluting with dichloromethane:methanol, 9:1. Combination and evaporation of the appropriate fractions gave a solid which was recrystallised from ethyl acetate-methanol to afford the title compound, m.p. 250°–252° (1.87 g), characterised spectroscopically to be identical to the product of Preparation 30.

Preparation 32

1-(4-Amino-3-cyano-5-methylphenyl)-2,4-dimethylimidazole

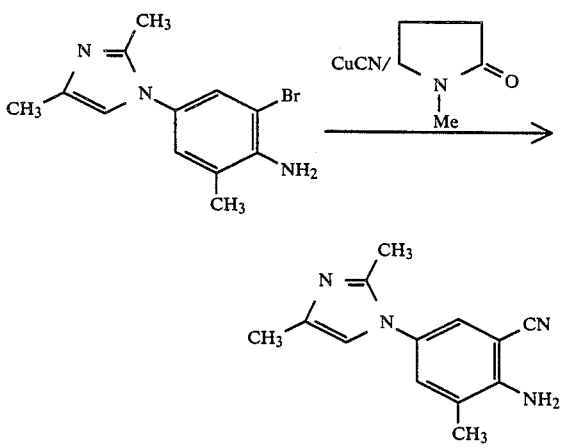

A mixture of 1-(4-amino-3-bromo-5-methylphenyl)-2,4-dimethylimidazole (17.3 g) and cuprous cyanide (17.9 g) was heated and stirred at 150° in N-methylpyrrolidone (50 cm³) for 6 hours. The cooled mixture was partitioned between ammonia solution (200 cm³; S.G. 0.880) and chloroform (200 cm³). The aqueous phase was extracted further with chloroform (2×100 cm³), and the combined and dried (MgSO₄) organic phases were evaporated in vacuo to give an oil, which was chromatographed on silica (Merck "MK 60.9385" [Trade Mark]), eluting with dichloromethane:methanol, 19:1. Combination and evaporation of the appropriate fractions gave an oil which was triturated with ether to give a solid (10.05 g). A small portion of this material was recrystallised from ethyl acetate-methanol to afford the title compound, m.p. 214°–217°.

Analysis %: Found: C,69.0; H,6.5; N,24.7; Calculated for $C_{13}H_{14}N_4$: C,69.0; H,6.2; N,24.8.

Preparation 33

4-(4-Amino-3-cyano-5-methylphenyl)-1,2,4-triazole, 0.25 H₂O, m.p. 283°–286°, was prepared similarly to the previous Preparation, using 4-(4-amino-3-iodo-5-methylphenyl)-1,2,4-triazole and cuprous cyanide as the starting materials.

Analysis %: Found: C,58.9; H,4.5; N,34.4; Calculated for $C_{10}H_9N_5 \cdot 0.25\ H_2O$: C,59.0; H,4.7; N,34.4.

Preparation 34

1-(4-Amino-3-bromo-5-methylphenyl)-2,4-dimethylimidazole. 0.5 H₂0

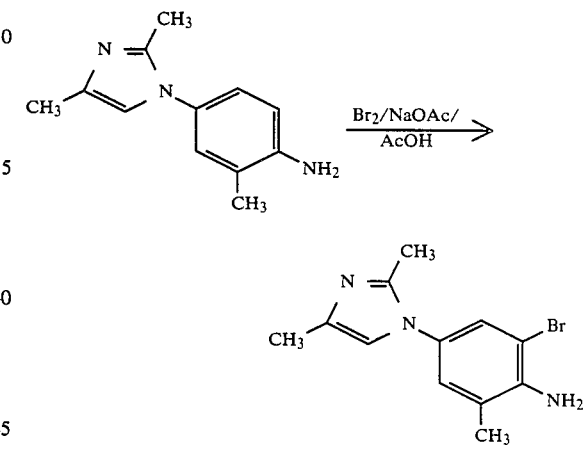

A solution of bromine (5.6 cm³) in glacial acetic acid (50 cm³) was added dropwise over 0.5 hours to a stirred solution of 1-(4-amino-3-methylphenyl)-2,4-dimethylimidazole (20.3 g) and sodium acetate (9.02 g) in glacial acetic acid (200 cm³). After a further 0.5 hours, volatile material was removed in vacuo, and the residue was partitioned between chloroform (200 cm³) and 10% aqueous sodium hydroxide solution (to pH 10). The aqueous phase was further extracted with chloroform (2×100 cm³) and the combined and dried (MgSO₄) organic extracts were evaporated in vacuo to afford a solid which was chromatographed on silica (Merck "MK 60.9385" [Trade Mark]) eluting with dichloromethane:methanol, 19:1. Combination and evaporation of the appropriate fractions gave an oil which was triturated with ether to afford the title compound, m.p. 176°–180.5°. The mother liquors were evaporated and the residue was rechromatographed on silica, as before, to give a further crop of material (total yield 17.3 g).

Analysis %: Found: C,49.5; H,5.0; N,14.4; Calculated for $C_{12}H_{14}N_3Br \cdot 0.5\ H_2O$: C,49.8; H,5.2; N,14.5.

Preparation 35

4-(4-Amino-3-iodo-5-methylphenyl)-1,2,4-triazole, m.p. 211°–214°, was prepared similarly to the previous Preparation, using 4-(4-amino-3-methylphenyl)-1,2,4-triazole, iodine monochloride and sodium acetate in glacial acetic acid, as the starting materials.

Analysis %: Found: C,35.8; H,3.1; N,18.4; Calculated for $C_9H_9IN_4$: C,36.0; H,3.0; N,18.7.

Preparation 36

1-(4-Amino-3-methylphenyl)-2,4-dimethylimidazole

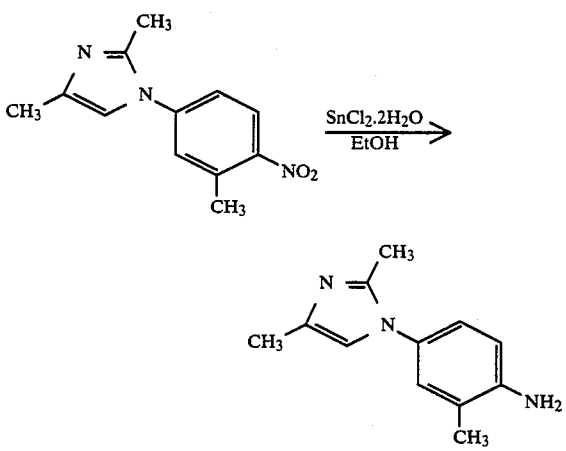

Stannous chloride dihydrate (40.7 g) was added portionwise to a stirred suspension of 1-(3-methyl-4-nitrophenyl)-2,4-dimethylimidazole (8.3 g) in absolute ethanol (100 cm³). After heating under reflux for 4 hours, the cooled mixture was basified to pH8 with aqueous 2.5M sodium hydroxide and filtered. The filtrate was evaporated in vacuo, partitioned between chloroform (200 cm³) and water (50 cm³), and the aqueous phase was further extracted with chloroform (2×100 cm³). The combined and dried (MgSO₄) organic extracts were concentrated in vacuo to give a solid (6.8 g) which was recrystallised from ethyl acetate to afford 1-(4-amino-3-methylphenyl)-2,4-dimethylimidazole, m.p. 92°–96°.

Preparation 37

4-(4-Amino-3-methylphenyl)-1,2,4-triazole

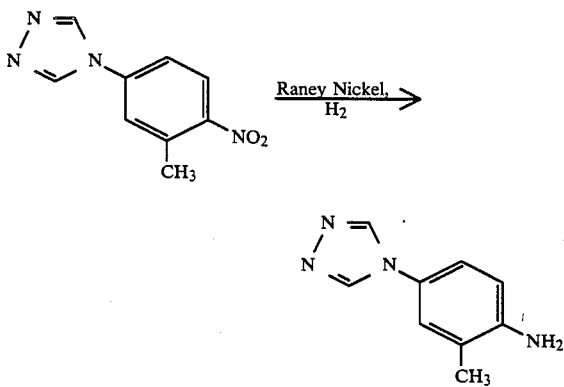

A solution of 4-(3 methyl-4-nitrophenyl)-1,2,4-triazole (1.0 g) in acetic acid (25 cm³) was hydrogenated at 25° and 60 p.s.i. (4.13×10⁵ Pa) pressure over Raney nickel (0.2 g) for 2 hours. The mixture was then filtered through "Solkafloc" (Trade Mark for a cellulose based filtering agent), the solvent was evaporated in vacuo and the residue was partitioned between chloroform (100 cm³) and aqueous sodium carbonate solution (20 cm³). The aqueous phase was further extracted with chloroform (3×50 cm³) and the combined and dried (MgSO₄) organic extracts were concentrated to afford an oil which was chromatographed on silica (Merck "MK 60.9385" [Trade Mark]) eluting with methanol:ethyl acetate, 1:9. Combination and evaporation of the appropriate fractions afforded a solid which was recrystallised from ethyl acetate/hexane to give 4-(4-amino-3-methylphenyl)-1,2,4-triazole, m.p. 152°–154° (0.67 g).

Analysis %: Found: C,62.0; H,5.6; N,31.8; Calculated for $C_9H_{10}N_4$: C,62.1; H,5.7; N,32.2.

Preparation 38

1-(3-Methyl-4-nitrophenyl)-2,4-dimethylimidazole

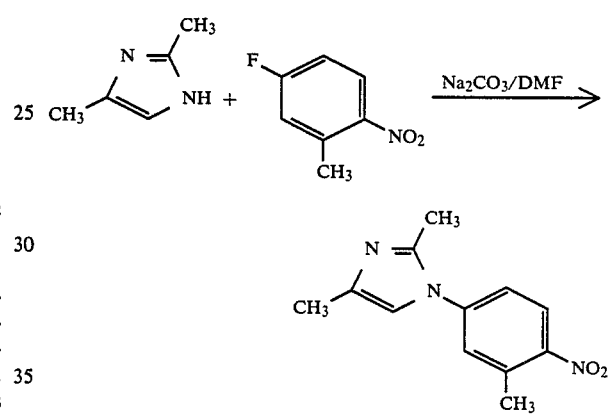

A mixture of 3-fluoro-6-nitrotoluene (10.3 g), 2,4-dimethyl-imidazole (6.36 g) and sodium carbonate (7.5 g) was heated with stirring in dimethylformamide (40 cm³) at 130° for 40 hours. The cooled mixture was then concentrated in vacuo, the residue was acidified to pH1 with 4M hydrochloric acid, and the resulting solution was extracted with chloroform (2×25 cm³) to remove any neutral material. The combined aqueous phases were basified to pH10 with 2.5M sodium hydroxide solution and the mixture was extracted with chloroform (3×250 cm³). The combined and dried (MgSO₄) organic extracts were concentrated in vacuo to give a solid which was chromatogrpahed on silica (Merck "MK 60.9385" [Trade Mark]) eluting with methanol:ethyl acetate, 1:19. Combination and evaporation of appropriate fractions afforded a solid (8.4 g) which was recrystallised from ethyl acetate to give 1-(3-methyl-4-nitrophenyl)-2,4-dimethylimidazole, m.p. 135.5°–138°.

Analysis %: Found: C,62.0; H,5.7; N,17.9; Calculated for $C_{12}H_{13}N_3O_2$: C,62.3; H,5.7; N,18.2.

Preparation 39

4-(3-Methyl-4-nitrophenyl)-1,2,4-triazole

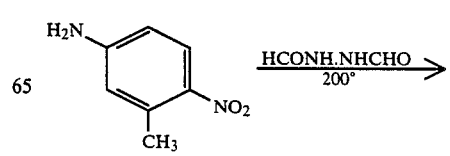

-continued

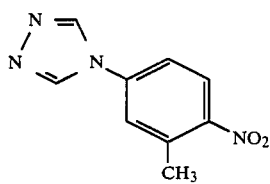

A mixture of 3-amino-6-nitrotoluene (2.0 g) and 1,2-diformyl-hydrazine (1.3 g) was heated under nitrogen for 1 hour at 200°. The residue was then cooled and chromatographed on silica (Merck "MK 60.9385" [Trade Mark]) eluting with methanol:dichloromethane, 1:19. Combination and evaporation of appropriate fractions gave a solid (1.03 g) which was recrystallised from ethanol to afford 4-(3-methyl-4-nitrophenyl)-1,2,4-triazole, m.p. 208°–210°.

Analysis %: Found: C,52.8; H,4.0; N,27.3; Calculated for $C_9H_8N_4O_2$: C,52.9; H,3.9; N,27.4.

Preparation 40

2-Amino-5-(2-Methoxypyrid-5-yl)-3-methylbenzylalcohol

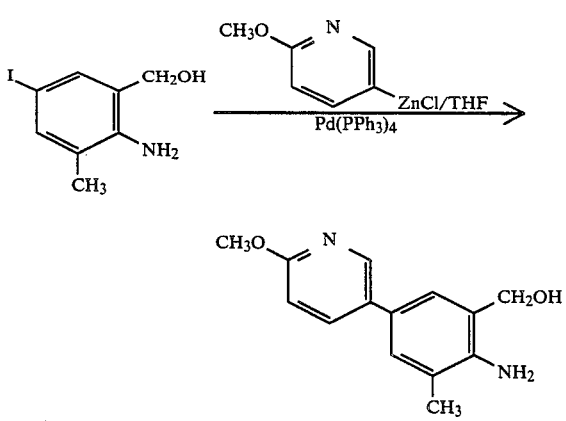

n-Butyllithium (33 cm³ of a 1.6M solution in n-hexane) was added to a stirred solution of 2-methoxy-5-bromopyridine (9.4g) in tetrahydrofuran (THF) (70 cm³) at −70° under nitrogen. After stirring for 1 hour at −70° the mixture treated with a solution of anhydrous zinc chloride (14.2 g) in THF (70 cm³) and the mixture was warmed to room temperature. 2-Amino-5-iodo-3-methylbenzyl alcohol (3.9 g—see preparation 8) and tetrakis(triphenylphosphine) palladium (0) (0.4 g) were added and the mixture heated under reflux for 3 hours. Saturated ammonium chloride solution (50 cm³) was added to the cooled solution and the mixture was partitioned between ethyl acetate (300 cm³) and a solution of ethylenediaminetetraacetic acid disodium salt (20 g) in water (300 cm³). The aqueous phase was further extracted with ethyl acetate (300 cm³) and the combined and dried (MgSO₄) organic phases were evaporated in vacuo to give a brown oil which was chromatographed on silica (Merck "MK 60.9385" [Trade Mark]) eluting with dichloromethane:methanol, 49:1. Combination and evaporation of appropriate fractions afforded the title compound as a waxy solid, m.p. 80°–82° (3.6 g), which was used directly without further purification.

Preparation 41

2-Amino-5-(2-methoxypyrid-5-yl)-3-methylbenzaldehyde

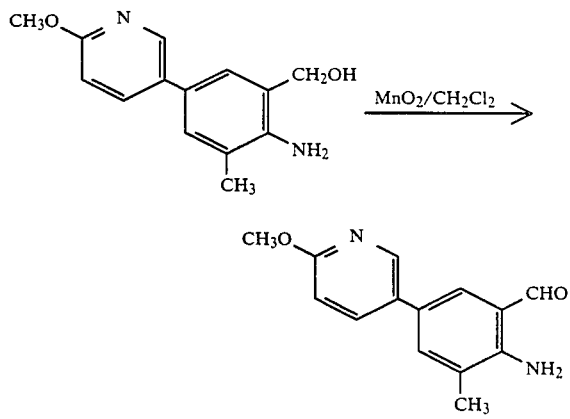

Freshly dried manganese dioxide (1.5 g) was added to a solution of 2-amino-5-(2-methoxypyrid-5-yl)-3-methylbenzyl alcohol (1.5 g) in dichloromethane (20 cm³) under nitrogen and the mixture was stirred for 2 hours at room temperature. The mixture was filtered, the filtrate evaporated to dryness, and the residue was chromatographed on silica (Merck "MK 60.9385" [Trade Mark])eluting with dichloromethane. Combination and evaporation of appropriate fractions afforded the title compound, m.p. 81°–84° (0.98 g).

Analysis %: Found: C,69.3; H,5.6; N,11.6; Calculated for $C_{16}H_{14}N_2O_2$: C,69.4; H,5.8; N, 11.6.

Preparation 42

2-Amino-3-methyl-5-(2-hydroxypyrid-5-yl)benzaldehyde.

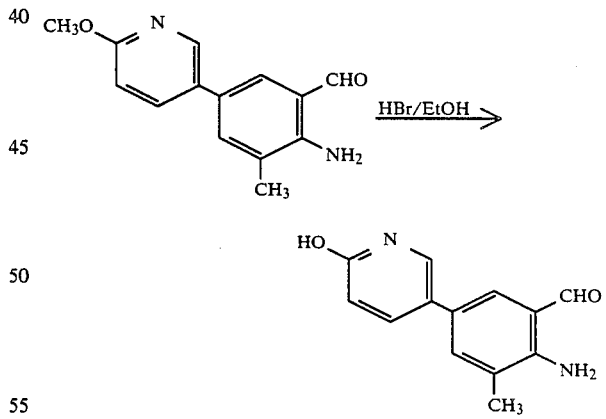

2-Amino-5-(2-methoxypyrid-5-yl)-3-methylbenzaldehyde (0.92g) was added to a stirred solution of hydrobromic acid (3 cm³ of a 60% w/w aqueous solution) in absolute ethanol (100 cm³) under nitrogen and the mixture was heated under reflux for 2 hours. The cooled solution was evaporated in vacuo, and the residue partitioned between 10% sodium carbonate solution (30 cm³) and dichloromethane (50 cm³). The organic phase was dried (MgSO₄) and evaporated in vacuo to give a solid residue which was chromatographed in silica (Merck "MK 60.9385" [Trade Mark]) eluting with dichloromethane:methanol, 10:1. Combination and evaporation of appropriate fractions followed by recrystallisation from ethyl acetate afforded the title compound, m.p. 231°–234° (0.26 g).

Analysis %: Found: C,66.9; H,5.8; N,11.1; Calculated for $C_{13}H_{12}N_2O_2.0.25\ CH_3CO_2Et$:C,67.2; H,5.6; N,11.2

Preparation 43

Ethyl N-(2-amino-3-methyl-5-[2-hydroxypyrid-5-yl]benzyl)-glycinate

The title compound was prepared similarly to Preparation 25 using ethyl glycinate and 2-amino-5-(2-hydroxypyrid-5-yl)-3-methylbenzaldehyde followed by hydrogen over Pd/C:

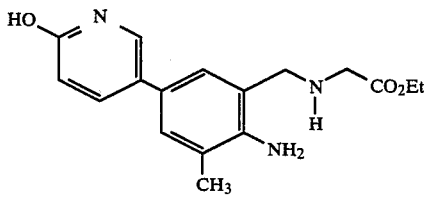

The product was isolated as a crude solid and was used directly without further purification.

We claim:

1. A tetrahydroimidazoquinazolinone compound of the formula:

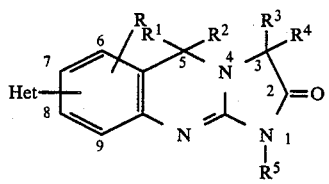

or a pharmaceutically acceptable salt thereof, wherein "Het" is a pyrrolyl, imidazolyl, pyrazolyl, triazolyl, tetrazolyl, pyridyl, pyrazinyl, pyrimidinyl, pyridazinyl, oxazolyl, isoxazolyl, thiazolyl, isothiazolyl, furyl, thienyl or oxadiazolyl group attached to the 6-, 7-, 8- or 9-positions of said 1,2,3,5-tetrahydroimidazo(2,1-b)quinazolin-2-(1H)-one ring, including the N-oxide derivatives of those groups which are nitrogen-containing, with all of said groups being optionally substituted with up to three substituents each independently selected from $C_1$–$C_4$ alkyl, $C_1$–$C_4$ alkoxy, hydroxy, hydroxymethyl, cyano, halogen, trifluoromethyl, ($C_1$–$C_4$ alkoxy)carbonyl, nitro, —$NR^6R^7$, —$CONR^6R^7$, —$SO_2NR^6R^7$ and —$S(O)_m(C_1$–$C_4$ alkyl) wherein $R^6$ and $R^7$ are each independently hydrogen or $C_1$–$C_4$ alkyl and m is zero, one or two; R is hydrogen, $C_1$–$C_4$ alkyl, $C_1$–$C_4$ alkoxy, hydroxy, hydroxymethyl, halogen or trifluoromethyl attached to the 6-, 7-, 8- or 9-positions of said 1,2,3,5-tetrahydroimidazo(2,1-b)quinazolin-2-(1H)-one ring; and $R^1$, $R^2$, $R^3$, $R^4$ and $R^5$ are each hydrogen or $C_1$–$C_4$ alkyl.

2. A compound as claimed in claim 1 wherein "Het" is attached to the 7-position of the tetrahydroimidazoquinazolinone ring.

3. A compound as claimed in claim 1 wherein "Het" is (a) an imidazolyl or triazolyl group optionally substituted with one or two $C_1$–$C_4$ alkyl groups, or (b) a pyridyl group optionally substituted with one or two $C_1$–$C_4$ alkyl groups or with a single hydroxy group.

4. A compound as claimed in claim 3 wherein the optionally substituted alkyl group is methyl.

5. A compound as claimed in claim 1 wherein R is hydrogen or a $C_1$–$C_4$ alkyl group at the 9-position of the tetrahydroimidazoquinazolinone ring.

6. A compound as claimed in claim 1 wherein $R^1$, $R^3$ and $R^4$ are each hydrogen or methyl, and $R^2$ and $R^5$ are each hydrogen.

7. A compound as claimed in claim 1 wherein "Het" is attached to the 7-position of the tetrahydroimidazoquinazolinone ring and is (a) an imidazolyl or triazolyl group optionally substituted with one or two $C_1$–$C_4$ alkyl groups, or (b) a pyridyl group optionally substituted with one or two $C_1$–$C_4$ alkyl groups or with a single hydroxy group; R is hydrogen or $C_1$–$C_4$ alkyl at the 9-position; and $R^1$, $R^3$ and $R^4$ are each hydrogen or methyl, and $R^2$ and $R^5$ are each hydrogen.

8. A compound as claimed in claim 7 wherein the optionally substituted alkyl group is methyl.

9. A compound as claimed in claim 7 wherein "Het" is a 2,4-dimethylimidazol-1-yl, 1,2,4-triazol-1-yl, 1,2,4-triazol-4-yl, 1-methyl-1,2,4-triazol-5-yl, 2,6-dimethylpyrid-3-yl or 2-hydroxypyrid-5-yl group, and R is hydrogen or methyl.

10. A compound as claimed in claim 9 wherein "Het" is 2,4-dimethylimidazol-1-yl, R is methyl and $R^1$, $R^3$ and $R^4$ are each hydrogen.

11. A compound as claimed in claim 9 wherein "Het" is 2,4-dimethylimidazol-1-yl, R is methyl, $R^1$ are $R^4$ are each hydrogen and $R^3$ is methyl.

12. A compound a claimed in claim 9 wherein "Het" is 1,2,4-triazol-4-yl, R is methyl and $R^1$, $R^3$ and $R^4$ are each hydrogen.

13. 7-(2,4-Dimethylimidazol-1-yl)-9-methyl-1,2,3,5-tetrahydroimidazo(2,1-b)quinazolin-2-(1H)-one.

14. A pharmaceutical composition comprising a pharmaceutically carrier or diluent and an effective cardiac-stimulating amount of a compound as claimed in claim 1.

15. The composition according to claim 14 wherein the compound is 7-(2,4-dimethylimidazol-1-yl)-9-methyl-1,2,3,5-tetrahydro(2,1-b)quinazolin-2-(1H)-one.

16. The composition according to claim 14 wherein the compound is 3,9-dimethyl-7-(2,4-dimethylimidazol-1-yl)-1,2,3,5-tetrahydroimidazo(2,1-b)quinazolin-2-(1H)-one.

17. The composition according to claim 14 wherein the compound is 9-methyl-7-(1,2,4-triazol-4-yl)-1,2,3,5-tetrahydroimidazo(2,1-b)quinazolin-2-(1H)-one.

18. A method for stimulating cardiac activity in the treatment of a subject afflicted with congestive heart failure, which comprises administering to said subject an effective cardiac-stimulating amount of a compound as claimed in claim 1.

19. The method as claimed in claim 18 wherein said compound is 7-(2,4-dimethylimidazol-1-yl)-9-methyl-1,2,3,5-tetrahydro(2,1-b)quinazolin-2-(1H)-one.

20. The method as claimed in claim 18 wherein said compound is 3,9-dimethyl-7-(2,4-dimethylimidazol-1-yl)-1,2,3,5-tetrahydroimidazo(2,1-b)quinazolin-2-(1H)-one.

21. The method as claimed in claim 18 wherein said compound is 9-methyl-7-(1,2,4-triazol-4-yl)-1,2,3,5-tetrahydroimidazo(2,1-b)quinazoline-2-(1H)-one.

* * * * *